(12) United States Patent
Song et al.

(10) Patent No.: US 9,880,078 B2
(45) Date of Patent: Jan. 30, 2018

(54) COMPOSITION FOR AGGREGATING BIOLOGICAL SAMPLE

(71) Applicant: National Cancer Center, Gyeonggi-do (KR)

(72) Inventors: Gang Won Song, Gyeonggi-do (KR); Geon Kook Lee, Seoul (KR)

(73) Assignee: NATIONAL CANCER CENTER, Gyeonggi-Do (KR)

( * ) Notice: Subject to any disclaimer, the term of this patent is extended or adjusted under 35 U.S.C. 154(b) by 1180 days.

(21) Appl. No.: 13/712,725

(22) Filed: Dec. 12, 2012

(65) Prior Publication Data

US 2014/0005075 A1 Jan. 2, 2014

(30) Foreign Application Priority Data

| Jan. 31, 2012 | (KR) | 10-2012-0009480 |
| Jun. 4, 2012 | (KR) | 10-2012-0060073 |
| Jun. 4, 2012 | (KR) | 10-2012-0060074 |
| Nov. 9, 2012 | (KR) | 10-2012-0126597 |

(51) Int. Cl.
| G01N 1/36 | (2006.01) |
| G01N 1/30 | (2006.01) |
| G01N 33/50 | (2006.01) |

(52) U.S. Cl.
CPC ........... *G01N 1/30* (2013.01); *G01N 33/5005* (2013.01); *G01N 33/5088* (2013.01); *G01N 1/36* (2013.01)

(58) Field of Classification Search
None
See application file for complete search history.

(56) References Cited

U.S. PATENT DOCUMENTS

| 4,880,660 A * | 11/1989 | Aasen | A61K 8/8152 |
| | | | 106/35 |
| 6,174,683 B1 | 1/2001 | Hahn et al. | |
| 2001/0039262 A1 * | 11/2001 | Venkataraman | A61K 31/401 |
| | | | 514/310 |
| 2005/0186361 A1 * | 8/2005 | Fukuda | G09B 23/30 |
| | | | 428/15 |

FOREIGN PATENT DOCUMENTS

| JP | 2007-046988 | 2/2007 |
| KR | 1020050046826 A | 5/2005 |
| KR | 1020090022639 A | 2/2009 |
| KR | 1020090097068 A | 9/2009 |
| KR | 1020100051294 A | 5/2010 |
| KR | 101150840 B1 | 6/2012 |
| WO | WO 2008/038813 A1 | 4/2008 |

OTHER PUBLICATIONS

Mobley et al., Surgical tissue adhesives, Facial Plast. Surg. Clin. N. Am., 10:147-154. 2002.
Ryou et al., Tissue Adhesives: A Revies, Techniques in Gastrotestinal Endoscopy, 33-37, 2005.
Charafe-Jauffret et al., "Gene expression profiling of breast cell lines identifies potential new basal markers," Oncogene, 25:2273-2284, 2006.
European Patent Application No. 12867600.4; Communication under Rule 71(3) EPC, Intent to Grant; May 19, 2017; 58 pages.

* cited by examiner

Primary Examiner — Christopher M Gross
(74) Attorney, Agent, or Firm — Lathrop Gage

(57) ABSTRACT

The present invention relates to a composition for aggregating biological sample used for manufacturing paraffin block for microscopic observation of biological sample, a method for preparing paraffin block using the same, and a method for microscopic observation of biological sample using the paraffin block, and particularly to a composition for aggregating biological sample including the first composite containing at least one water-soluble polymer selected from the group comprising polyvinyl alcohol, polyethylene oxide, polyacrylamide, polyvinylpyrrolidon, polyacrylic acid, polyethyleneimine, polyamines, polyamideamine, and polydiallyl dimethylammonium chloride and distilled water; and the second composite containing at least one organic solvent selected from the group comprising alcohol, xylene, and acetone and at least one medical adhesive selected from the group comprising cyanoacrylate, fibrin glue, protein glue, polyurethane, and sealant containing PEG (polyethylene glycol), a method for preparing paraffin block using the same, and a method for microscopic observation of biological sample using the prepared paraffin block.

8 Claims, 17 Drawing Sheets

IHC: H&E  (a)

IHC: CerbB2- (b)

FISH: *HER2-* (c)

SISH: *HER2-* (d)

COMPOSITION FOR AGGREGATING BIOLOGICAL SAMPLE

BACKGROUND OF THE INVENTION

1. Technical Field

The present invention relates to: a composition used in preparing paraffin block by collecting biological tissues, biological fluids, or single cells and preparing them to a mass, assemblage and formation for microscopic observation, biomonitoring, test, disease diagnosis, prediction, verification, detection, confirmation or selection, and disease monitoring (hereinafter, 'a composition for aggregating biological sample'); a method for preparing paraffin block using the composition for aggregating biological sample for study of the sample; and a method for microscopic observation of the biological sample aggregated by the composition for aggregating biological sample and fixed in the paraffin block to distinguish between tissues with and without disease, and cells with and without disease.

In addition, the present invention relates to a method for preparing cell block for cellular microarray including a process to aggregate biological samples such as tissue cells and cultured cells using the composition for aggregating biological sample and a cell block for cellular microarray prepared by the same.

Using the composition for aggregating biological sample of the present invention, it is possible to improve accuracy of histological and cytological diagnosis for extremely small amount and fluid sample and improve the cell block technique to higher quality cell block technique in order to allow conservative diagnostic approaches by maintaining antigenicity of the paraffin block prepared from the sample.

2. Description of the Related Art

Histological or cytological examination not only takes a very important position in laboratory medicine but also plays an important role in making a final decision of clinical disease diagnosis or studying disease. Pathological examination is an examination that isolates or aspirates human tissue suffering a disease to identify the name of disease such as cancer through microscopic observation. The histological or cytological examination is based on observing and judging morphological changes of cells or tissues different from other laboratory methods. Nowadays, a lot of efforts have been given to obtain these data and for this, various special methods have been used according to a trend wanting to get objective data.

Especially recently, histochemical examination, immunohistochemistry, special staining, and molecular pathological examination have appeared to increase accuracy of objective diagnosis. For accurate diagnosis of diseases and study on proper therapies for them, it is important to observe morphological findings of biological sample collected from lesions. In order to observe these morphological changes, researchers use hematoxylin-eosin staining specimen basically. However, because various diseases has been increasingly segmented, new diagnostic techniques have been being introduced increasingly, and a lot of tumor markers helpful to tumor diagnosis and more prognostic factors able to predict prognosis have got known, it is difficult to obtain comprehensive information with conventional hematoxylin-eosin staining specimen. Examination methods for complementing these problems include immunohistochemical staining method and molecular pathologic evaluation. Among these, the immunohistochemical staining is being used efficiently for identifying the origin of undifferentiated cell, determining existence of enzyme, hormone, tumor marker, and prognostic factor, discriminating between carcinoma and sarcoma, discriminating between benign tumor and malignant tumor, and presuming primary lesion of metastatic cancer. It is highly sensitive and specific examination method, which has been used as an essential examination method in diagnostic pathology and morphological study for the last 20~30 years.

Diagnostic cytology is a field of pathology to determine existence or contents of a lesion in aspects of morphology based on cytological findings, which refers to a clinical laboratory medicine to interpret microscopically cells exfoliated naturally from various regions of human body by several clinical manipulations or cells detached from tissue surface or inside with an instrument. The diagnostic cytology includes: i) spontaneous exfoliative diagnostic cytology that smears cells exfoliated spontaneously by normal or pathological causes on a slide and then observes them with a microscope after fixation and staining; ii) aspiration biopsy diagnostic cytology that aspirates cells by injecting a fine needle attached syringe into the lesion, collects cells by compulsion, smears them on a slide, and observes them with a microscope after fixation and staining; iii) touch print diagnostic cytology that makes a slide contact directly to a lesion visible with naked eyes, smears cells on it, and then observes them with a microscope after fixation and staining; iv) cell smear examination that smears target cells collected on a slide thinly and then observes them with a microscope; v) cell block technique that prepares paraffin embedded cell block by infiltrating paraffin into cellular sediments collected from liquid specimen; and vi) sputum examination. Among the diagnostic cytological methods, the cell block technique retains superior merits to other methods and keeps remarkable diagnostic values in the points that is capable of special staining to identify other cell products, bacteria and fungi, preparing fluid specimen, observing diagnostic evidences which is impossible to observe them in other methods.

In application of the cell block method, the liquid sample is collected from various regions of human body and concretely, the effluents from respiratory tract, gastrointestinal system, and urinary system is made to the cell block by fixing in a fixative at first and then prepared to the paraffin block. The conventional methods to prepare cell block that have been used include: i) a fixed sediment method using sedimentation with centrifuging and formalin; ii) an egg albumin method using a principle that the egg albumin is coagulated in ethanol; iii) an agar method; iv) a plasma thrombin clot method; v) collodion bag method; and vi) Millpore filter method.

However, these traditional methods actually cannot get satisfactory results because of several problems including difficulty in slide interpretation from background staining, contraction of sample supporting agar in the method using agar gel, time required for preparing paraffin block and high cost.

Besides, while the paraffin block method has been used for the purpose of diagnosis, treatment and study through understanding of shapes of tissue and cells, special staining and immunohistochemical staining from it, it has been difficult or impossible to prepare the paraffin block when the quantity of collected cells was extremely little or the sample is extremely small. In addition, when preparing a paraffin block from tissue or cellular suspension with centrifuging, there have been some problems also, including that because of small size or quantity of tissue, the tissue or cells were dispersed, discrimination with paraffin was difficult, and paraffin embedding with a pincette was impossible.

Korea Public Patent Notification No. 2009-97068 describes a composition of embedding resin for histological analysis of scaffold for tissue engineering and a slide preparing method by the same and concretely, describes a method including following steps: performing melt blending of ethylene vinyl acetate copolymer containing paraffin and vinyl acetate as 1-80% at 40-100° C. to 2-50%; and then making the paraffin and ethylene derived copolymer blended solution infiltrated by adding a sample to the melt.

In addition, Japan Public Patent Notification No. 2007-046988 describes a method for preparing embedded block for biological tissue specimen and information label for the embedded block, Korea Public Patent Notification No. 2005-46826 describes a method of using laser capture microdissection (LCM) extracted in pure RNA that obtained from paraffin block through tissue specific fixing agent, and WO 08/038813 describes a method to perform deparaffinization process from paraffin embedded specimen and analyze it.

Besides, the cellular microarray means an experimental system to obtain multiple information on genetic and protein alteration in different cell and their interaction by analyzing antibodies, proteins, lipids, or staining substances using cell block specimen where different kinds or tissues or cultured cells were arrayed on a solid scaffold Chen D S et al, Curr Opin Chem Biol (2006), 10:28-34]. Generally, as the specimen for cellular microarray is prepared by making block and sectioning after microarray of cell pellets obtained from cell bock prepared in the in a fixed case, the results depends on aggregation and embedding process in the cell block preparing process largely.

As shown in several studies on preparation of cell block relating to cellular microarray including Waterworth A et al, In Vitro Cell DevBiolAnim (2005), 41(7):185-187 and US Patent Publication No. 2010/0323907, 2006/0160169, and 2003/0157523, there were only cellular microarray techniques by paraffin infiltration or frozen section after fixation with formalin or agar in general methods, studies on methods for preparing cell block to solve the problems were actually insufficient.

Therefore, it is required constantly to develop a method for preparing cell block for cellular microarray able to satisfactory multiple diagnostic information for cells with small quantity or size.

SUMMARY OF THE INVENTION

Therefore, an object of the present inventions is to provide a composition for aggregating biological sample, a method for preparing paraffin block using the same, and a method for microscopic observation of biological sample using the paraffin block aggregated by the composition for aggregating biological sample and fixed in the paraffin block to distinguish between tissues with and without disease, and cells with and without disease, which can minimize loss or damage of sample, reduce background staining, simplify paraffin block preparing process, save time and cost required for preparing the paraffin block, improve the quality of slide sectioned from the paraffin block, and optimize areas for microscopic observation, because the preparing process of mass, assemblage, and formation of sample (hereinafter 'sample complex') is done in a centrifuge tube in preparing a paraffin block for microscopic observation, biomonitoring, test, pathological diagnosis, prediction, verification, detection, confirmation, discrimination, and disease monitoring using biological samples such as extremely small amount of biological tissues, biological fluids, or single cells by solving problems of the conventional methods.

Another object of the present invention is to provide a method for preparing cell block for cellular microarray, which can minimize problems such as loss of sample and background staining and facilitate economic process of preparing the cell block in microarray analysis on extremely small amount of fluid cells, tissue cells, or cultured cells and a cell block for cellular microarray prepared by the same.

In one aspect, the present invention provides the composition for aggregating biological sample including: the first composite containing at least one water-soluble polymer selected from the group comprising polyvinyl alcohol, polyethylene oxide, polyacrylamide, polyvinylpyrrolidon, polyacrylic acid, polyethyleneimine, polyamines, polyamideamine, and polydiallyldimethylammonium chloride and distilled water; and the second composite containing at least one organic solvent selected from the group comprising alcohol, xylene, and acetone and at least one medical adhesive selected from the group comprising cyanoacrylate, fibrin glue, protein glue, polyurethane, and sealant containing PEG (polyethylene glycol).

According to an example of the present invention, the water soluble polymer is polyvinyl alcohol; the organic solvent is acetone; and the medical adhesive is cyanoacrylate.

According to another example of the present invention, the first composite may include carboxymethyl cellulose and dimethyl sulfoxide also and the second composite may include concentrated formalin also.

In addition, according to another example of the present invention, the first composite may include 1.5~2.0 part by weight of the water soluble polymer against 100 part by weight of distilled water.

According to another example of the present invention, the first composite may be used as content of 300~500 part by weight against 100 part by weight of sample to be aggregated.

According to another example of the present invention, the second composite may include 100~200 µl of a medical adhesive against 100 mL of an organic solvent.

According to another example of the present invention, the second composite may be used as content of 300~500 part by weight against 100 part by weight of the sample to be aggregated.

In another aspect, the present invention provides a method for preparing paraffin comprising several steps:
centrifuging the fixed biological sample, removing supernatant, and then obtaining sample sediment;
adding the first composite containing at least one water-soluble polymer selected from the group consisting of polyvinyl alcohol, polyethylene oxide, polyacrylamide, polyvinylpyrrolidon, polyacrylic acid, polyethyleneimine, polyamines, polyamideamine, and polydiallyldimethylammonium chloride and distilled water to the sediment to prepare the first sample solution;
adding the second composite containing at least one organic solvent selected from the group consisting of alcohol, xylene, and acetone and at least one medical adhesive selected from the group comprising cyanoacrylate, fibrin glue, protein glue, polyurethane, and sealant containing PEG (polyethylene glycol) to the first sample solution to prepare the second sample solution;
centrifuging the second sample solution, removing supernatant, and then obtaining the aggregated sample sediment; and subjecting the aggregated sample sediment to the spontaneous infiltration process to prepare paraffin block.

According to an example of the present invention, the water soluble polymer is polyvinyl alcohol; the organic solvent is acetone; and the medical adhesive is cyanoacrylate.

According to another example of the present invention, the first composite may include carboxymethyl cellulose and dimethyl sulfoxide additionally and the second composite may include concentrated formalin additionally.

In addition, according to another example of the present invention, fixation of the sample may be performed by using formalin or alcohol.

According to another example of the present invention, the first composite may include 1.5~2.0 part by weight of the water soluble polymer against 100 part by weight of distilled water; the second composite may include 100~200 µl of the medical adhesive against 100 mL of the organic solvent; and the above first composite and the above second composite may be used as 300~500 part by weight against 100 part by weight of the above sample.

According to another example of the present invention, when sample aggregation is observed after addition of the above second composite, the above second sample solution can be stirred.

According to another example of the present invention, the above spontaneous infiltration process can be performed by treating the above aggregated sample sediment wrapped by paper with alcohol, xylene, and paraffin successively.

According to another example of the present invention, the above treatment of each of alcohol, xylene, and paraffin may be performed multiple times.

In yet another aspect, the present invention provides a method for microscopic observation of biological sample including: performing microsection of the above paraffin block; and staining and observing the microsection of paraffin block with a microscope.

In still another aspect, the present invention provides a method for preparing cell block sample for cellular microarray including several steps comprising: 1) collecting and fixing the different cellular samples to be observed; 2) treating an organic solvent containing a medical adhesive and a water soluble solution containing a water-soluble polymer to the fixed cell sediment to obtain cell aggregate; 3) embedding the above cell aggregate to obtain a cell block; 4) stamping out the above embedded cell pellets from the above cell block and arraying them in a fixed frame; and 5) making the above arrayed frame to a block or a section.

According to an example of the present invention, the above medical adhesive may include at least one selected from the group comprising cyanoacrylate, fibrin glue, protein glue, polyurethane, and sealant containing PEG.

According to another example of the present invention, the above organic solvent may include at least one selected from the group comprising alcohol, xylene, acetone or their combinations.

According to another example of the present invention, the above water-soluble polymer may include at least one selected from the group comprising polyvinyl alcohol (PVA), polyethylene oxide, polyacrylamide, polyvinylpyrrolidon, polyacrylic acid, polyethyleneimine, polyamines, polyamideamine, and polydiallyldimethylammonium chloride.

According to another example of the present invention, the above medical adhesive may be cyanoacrylate; the above organic solvent may be acetone; and the above water-soluble polymer may be polyvinyl alcohol (PVA).

According to another example of the present invention, the above cyanoacrylate may be ethyl-2-cyanoacrylate.

In addition, in order to achieve the other task, the present invention provides a cell block for cellular microarray prepared by the above method.

EFFECTS OF INVENTION

According to the present invention, because when preparing a paraffin block with an extremely amount of fluid sample such as tissues or cell, the sample combines with a water-soluble polymer and a medical adhesive firmly and forms a sample complex, it is possible to minimize loss or damage of sample, facilitate the preparing process of paraffin block, save time and cost required for preparing the paraffin block, optimize the observation area in microscopic observation of the sample because physical and chemical property and adhesiveness of the water-soluble polymer supports the sample; reduce background staining and improve the quality of slide dissected from the paraffin block due to physical and chemical properties of the water-soluble polymer.

In addition, the method for preparing cell block for cellular microarray including a process to aggregate samples such as tissue cells and cultured cells by treating an organic solvent containing a medical adhesive and a solution containing a water-soluble polymer, can minimize loss of the sample and prepare the cell block for cellular microarray with shape stability and good aggregation of the cells through efficient and economic process even though it is performed to extremely small amount of fluid sample.

Therefore, the composition for aggregating biological sample, the method for preparing paraffin block using the same, and the method for preparing cell block sample for microarray can be used in and applied to histochemical examination, immunohistochemistry, in situ hybridization, cell culture, molecular study, and observation with an electron microscope.

DETAILED DESCRIPTION OF THE INVENTION

Figure 1:
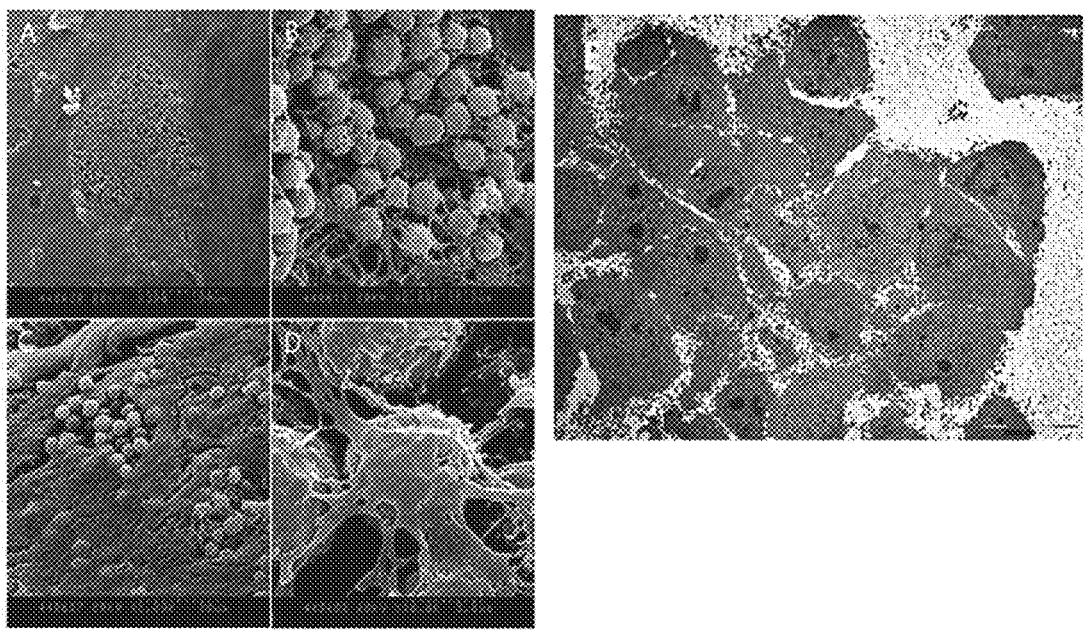
FIG. 1 is a SEM (Scanning Electron Microscope) and TEM (Transmission Electron Microscope) image of A549 cells aggregated by the composition for aggregating biological sample according to an example of the present invention.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

The present invention provides a composition for aggregating biological sample including water-soluble polymer, distilled water, organic solvent, and medical adhesive, a method for preparing paraffin block using the same, and a method for microscopic observation of biological sample using the above paraffin block. In addition, the present invention provides a method for preparing cell block for cellular microarray including a process to aggregate cellular samples such as tissue cells or cultured cells.

The composition for aggregating biological sample according to the present invention includes the first composite and the second composite, wherein the above first composite includes at least one water-soluble polymer selected from the group comprising polyvinyl alcohol, polyethylene oxide, polyacrylamide, polyvinylpyrrolidon, polyacrylic acid, polyethyleneimine, polyamines, polyamideamine, and polydiallyldimethylammonium chloride and distilled water.

Preferably, the above first composite includes polyvinyl alcohol and distilled water and more preferably includes carboxymethyl cellulose and dimethyl sulfoxide also other than the polyvinyl alcohol and the distilled water.

The above water-soluble polymers are specific polymeric substances soluble in water, which can be considered as highly applicable attractive substances because they can be applied to broad purposes from highly intensive fibers to medical materials by adjusting molecular variables and extremely various forms from atactic low molecular weight polymer with low price to stereoregular high molecular weight polymer with high cost. Especially, the polyvinyl alcohol and the polyethylene oxide have traits that they are not dissolved well in organic solvents such as alcohol, xylene, and acetone and dissolved well in water, which is because the polyvinyl alcohol and the polyethylene oxide have —OH residue, a hydrophilic residue, in their molecular structure.

In the present invention, chemical features of these water-soluble polymers were applied to the composition for embedding biological sample. In other words, because the above water-soluble polymers such as polyvinyl alcohol and polyethylene oxide have characteristics that they are not dissolved well in organic solvents such as alcohol, xylene, or paraffin and are dissolved well in water, when using water-soluble polymer solution where water-soluble polymers such as polyvinyl alcohol and polyethylene oxide are dissolved in distilled water with alcohol, xylene, or acetone for aggregating biological sample, the biological sample and the water-soluble polymer form a complex in aggregation, so they are deposited and get harder in centrifuge.

For this sample complex, water-soluble polymer in the complex will be removed in flowing water due to physical property contained by the water-soluble polymer and the biological sample to be observed will be remained alone on a glass slide in following staining process, so it will cause no inconvenience at all in the staining using that.

In addition, the carboxymethyl cellulose of the present invention is formed by substituting hydroxy residue (cellulose-OH) on C6 of glucose residue forming the cellulose with carboxymethyl residue (—CH$_2$COOH) and those formed by substituting more than 40% of the above hydroxy residue with carboxymethyl residue are dissolved in water to form a stable gel. These carboxymethyl celluloses have been used for researches such as isolation and purification of protein as thickening or stabilizing agents. They play a role in assisting for the water-soluble polymers to form a complex with biological sample.

Moreover, the dimethyl sulfoxide of the present invention is a non-protic polar solvent, which is generally used in study on organic reaction and organic synthesis and in the present invention, it makes separation of the biological sample, and the water-soluble polymer more difficult by strengthening the binding of both parties when they form a complex.

The content ratio by ingredients of the above first composite may include 1.5~2 part by weight against 100 part by weight of distilled water, wherein when the content of water-soluble polymer exceeds the above range, there is a problem that maldistributed aggregation of the sample may occur and when the content is below the above range, there is a problem that cohesive power of the sample may be weakened.

In addition, the above first composite may be used as content of 300~500 part by weight against 100 part by weight of the sample to be aggregated, wherein when the first composite exceeds the above content, there is a problem that it may cause insignificant breakdown of the sample because of excessive aggregation and when it is below the above range, it is also undesirable because the aggregation of biological sample may be weakened or delayed.

Besides, the composition for aggregating biological sample of the present invention is the second composite also as well as the first composite, wherein the above second composite includes at least one organic solvent selected from the group comprising alcohol, xylene, and acetone and at least one medical adhesive selected from the group comprising cyanoacrylate, fibrin glue, protein glue, polyurethane, and sealant containing PEG (polyethylene glycol).

As mentioned above, the water-soluble polymers such as polyvinyl alcohol and polyethylene oxide have characteristics that although they are dissolved well in water, they are rarely dissolved in organic solvents such as alcohol and xylene and seldom deteriorated during storing. Especially, the polyvinyl alcohol tends to be aggregated and form white precipitate when shaking the mixture after addition of acetone. In the present invention, it was intended to form aggregated sample sediment by adding the second composite including acetone to the sample complex formed by using the above first composite, applying theses chemical characteristics of acetone, polyvinyl alcohol, polyethylene oxide and/or cyanoacrylate to make the above sample complex aggregated. The above aggregated sample sediment may be altered to solid pellet through future centrifuge process and preparing paraffin block by performing will be possible by further process on the pellet.

Additionally, the cyanoacrylate known as medical glue or adhesive has been used in wide applications from packaging of medical device, gluing or adhesion for surgery, to hemostasis and has characteristics such as biocompatibility, biodegradability, and sterility. Especially, the cyanoacrylate is featured by being polymerized and solidified instantly when contacting with water or weak base and in the present invention, it was intended to further facilitate aggregation of the sample complex formed with the first composite by applying this chemical characteristics of cyanoacrylate contained in the second composite.

The above second composite may include 100~200 μl of medical adhesive against 100 mL of organic solvent, wherein when the content of medical adhesive exceeds the above range, there is a problem that some crystals may remain on the glass slide insignificantly during washing it with water in staining it after preparing the paraffin block and when its content is below the range, there is a problem that binding force may be weakened in forming the sample complex. Particularly, 95-96% (v/v) of cyanoacrylate is preferable to the above medical adhesive.

In addition, the above second composite may be used as content of 300~500 part by weight against 100 part by weight of the sample to be aggregated, wherein when the content of the second composite exceeds the above range, there is a problem that the sample aggregation complex may become larger than the amount of sample and when its content is used as below the range, there is a problem that the aggregate supporting the sample may be insufficient.

FIG. 1 illustrates a SEM (Scanning Electron Microscope) image of lung adenocarcinoma A549 cells aggregated by the composition for aggregating biological sample according to the present invention. The spherical shapes indicate lung adenocarcinoma A549 cells and the aggregated materials indicate the composition for aggregating biological sample according to the present invention. As shown in the above FIG. 1, it became possible to aggregate even cells that had been difficult to be aggregated traditionally by using the composition for aggregating biological sample according to the present invention. More detailed explanation will be presented in following examples.

The present invention provides the method for preparing paraffin using the above composition for aggregating biological sample, which includes: centrifuging the fixed biological sample, discarding supernatant, and then obtaining sample sediment;

adding the first composite containing at least one water-soluble polymer selected from the group comprising polyvinyl alcohol, polyethylene oxide, polyacrylamide, polyvinylpyrrolidon, polyacrylic acid, polyethyleneimine, polyamines, polyamideamine, and polydiallyldimethylammonium chloride and distilled water to the above sediment to prepare the first sample solution;

adding the second composite containing at least one organic solvent selected from the group comprising alcohol, xylene, and acetone and at least one medical adhesive selected from the group consisting of cyanoacrylate, fibrin glue, protein glue, polyurethane, and sealant containing PEG (polyethylene glycol) to the above first sample solution to prepare the second sample solution;

centrifuging the above second sample solution, discarding supernatant, and then obtaining aggregated sample sediment; and performing spontaneous infiltration process to the above aggregated sample sediment to prepare paraffin block.

Figure 2:
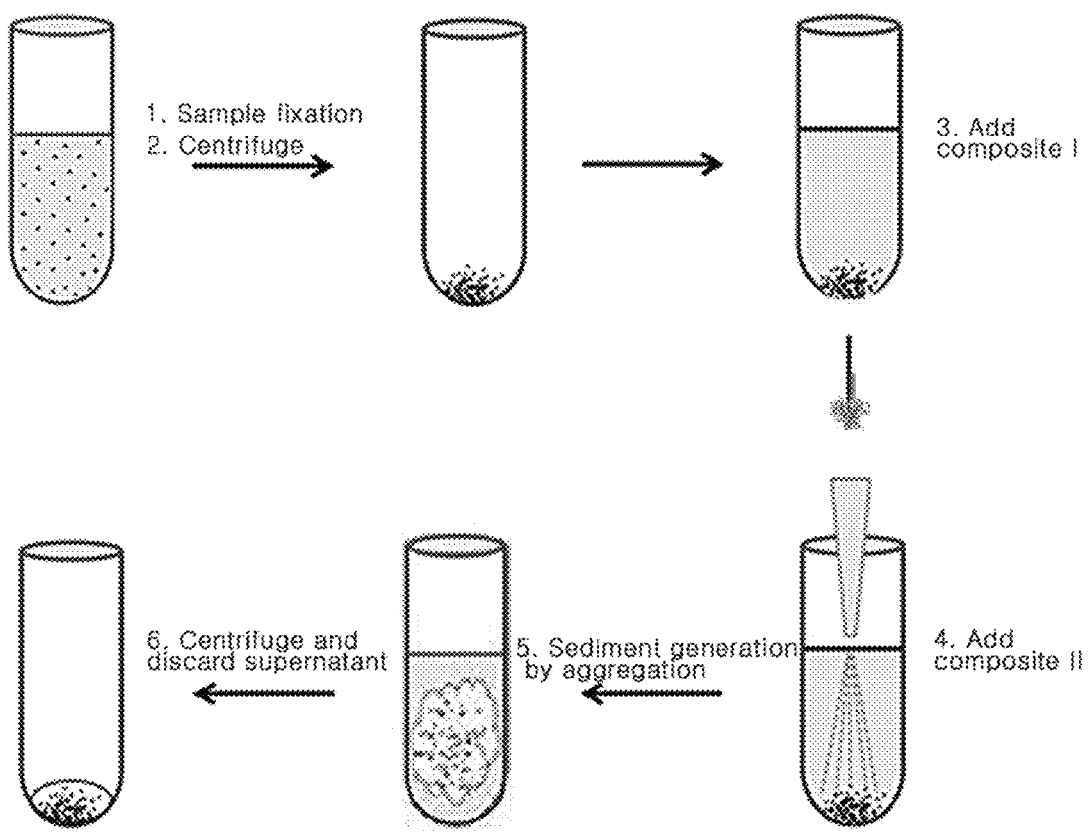
FIG. 2 is a brief process flowchart illustrating the method for preparing paraffin block according to the present invention.

FIG. 2 is a brief process flowchart illustrating the method for preparing paraffin block according to the present invention. As shown in FIG. 2, cells or other samples are fixed with fixative (Step 1). This fixation step of sample may be performed by methods commonly used in this industry such as using formalin or alcohol, but is not limited in these.

Then, the fixed sample with small amount or small size is separated into supernatant and sample sediment via centrifuging and after the separation, the supernatant is discarded and the sample sediment is obtained (Step 2). Particularly, it is preferable to discard it carefully, avoiding loss of the sample sediment during discarding the supernatant.

Subsequently, the first composite among the composition for aggregating biological sample according to the present invention is added to the sample sediment obtained after discarding the supernatant (Step 3), wherein the first composite may include at least one water-soluble polymer selected from the group comprising polyvinyl alcohol, polyethylene oxide, polyacrylamide, polyvinylpyrrolidon, polyacrylic acid, polyethyleneimine, polyamines, polyamideamine, and polydiallyldimethylammonium chloride and distilled water, include 1.5~2.0 part by weight against 100 part by weight of distilled water, and be used as content of 300~500 part by weight against 100 part by weight of the sample to be aggregated.

Especially for the amount of the first composite to be added, when the sample volume is sufficient, using small amount of it makes no difference, but when the sample volume is extremely small, it is desirable to use large amount of it, considering the block size in future preparing paraffin block.

To the above solution obtained by adding the first composite to the sample sediment (referring it as "the first sample solution" in this description for convenience of explanation), a step to add the second composite according to the present invention relatively quickly is performed as next step (Step 4).

The above second composite, as mentioned above, may include at least one organic solvent selected from the group comprising alcohol, xylene, and acetone and at least one medical adhesive selected from the group comprising cyanoacrylate, fibrin glue, protein glue, polyurethane, and sealant containing PEG (polyethylene glycol), preferably may include 100~200 μl of the above medical adhesive, and may be used as content of 300~500 part by weight against 100 part by weight of the sample to be aggregated. Through this process, the sample is aggregated to form a sediment in the solution obtained by addition of the above second composite (referring as "the second sample solution" in this description for convenience of explanation).

Preferably, when sample aggregation is observed after addition of the above composition for aggregating biological sample, mixing of the first sample solution and the second composite may be facilitated and further promotion of the aggregation may be resulted in by tapping lightly the sample aggregation solution (Step 5).

As next step, when performing centrifuge of the above second sample solution, the sediment is further aggregated to the bottom of container (Step 6), and finally, the sample sediment according to the present invention is prepared by discarding the supernatant, obtaining the aggregated sample sediment, and then performing infiltration to the obtained sample sediment.

The above mentioned spontaneous infiltration process may be performed by treating alcohol, xylene, and paraffin to the aggregated sample sediment wrapped with paper in order. Basic reasons requiring the above spontaneous infiltration include followings. Namely, in order to perform micro-section of tissue or cells to be observed with a microscope, it is required to remove water from the tissue or cells fixed in a fixative, using alcohol to enable paraffin to infiltrate (alcohol treatment step).

Next, because even though the moisture in the sample is removed by alcohol treated, the alcohol and the paraffin is seldom mixed each other, so it is required to remove alcohol using xylene (xylene treatment step).

Finally, it is required to perform micro-section of the sample for microscopic observation, so alcohol removal and paraffin infiltration in the sample specimen should be conducted (paraffin treatment step).

At this time, the alcohol treatment step may be performed by dividing several phases, for instance, it may be performed in a manner of treating low conc. of alcohol at first (capable of multiple times) and subsequently treating high conc. of alcohol (capable of multiple times). This multiple times of application may be applied identically to the xylene treatment step and paraffin treatment step.

In addition, the present invention provides the method for microscopic observation of biological sample using the paraffin block prepared by the above mentioned method, wherein the method includes steps performing micro-section of the paraffin block prepared by the above mentioned method, staining and observing the microsection of paraffin block. The above micro-section step may be performed by conventional microsection devices such as microtome and the above staining process may be conducted by using staining reagents used commonly in this industry. Especially, for the paraffin block according to the present invention, the water-soluble polymers are reacted with water to form water-soluble polymer, water and acetic acid due to physical properties of the water soluble polymer contained in the paraffin block. Therefore, there is a merit that when removing the water-soluble polymer and acetic acid with flowing water, only the sample exists on the glass slide to be observed and eventually they give no interference to staining.

Figure 14:
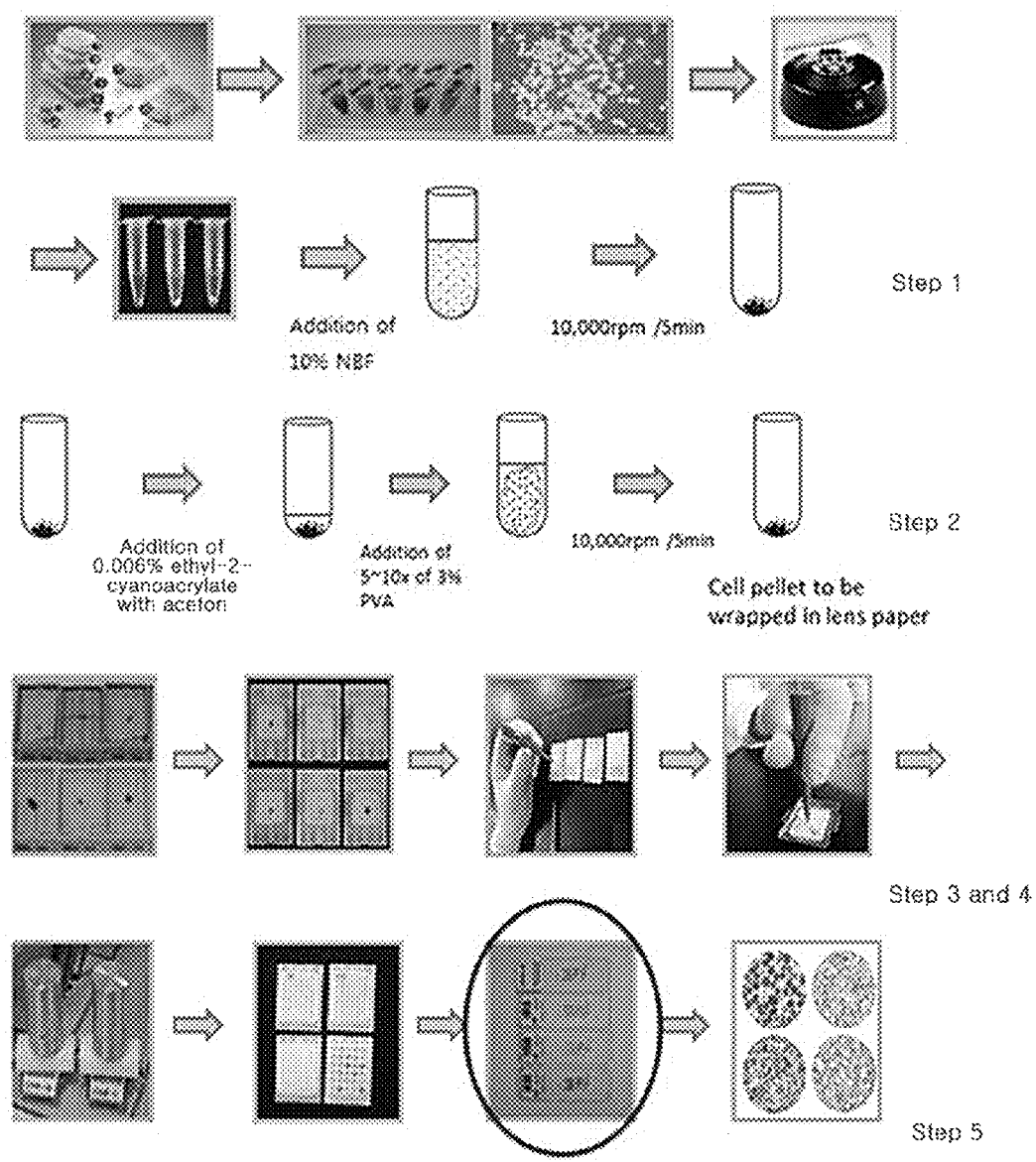
FIG. 14 is a flowchart to explain processes for preparing cell block for microarray according to another example of the present invention.

Besides the present invention provides a method for preparing cell block for cellular microarray using the paraffin block of biological sample, which as shown in FIG. 14 includes several steps comprising: 1) a step to collect and fix the different cellular samples to be observed (step 1 of FIG. 14); 2) a step to obtain cell aggregate by treating an organic solvent containing a medical adhesive and a water soluble solution containing a water-soluble polymer to the above fixed cell sediment (step 2 of FIG. 14); 3) obtain a cell block by embedding the above cell aggregate (step 3 of FIG. 14); 4) a step to stamp out the above embedded cell pellets from the above cell block and array them a fixed frame (step 4 of FIG. 14); and 5) a step to make the above arrayed frame to a block or a section (step 5 of FIG. 14).

The cellular samples may be tissue cells or culture cells, wherein for the tissue cells, cells exfoliated spontaneously or isolated from tissues by several clinical procedures such as surgery or treatment or using instruments may be used and for the cultured cells, cell lines may be used mainly. The process to collect cultured cells may be performed according to conventional methods in this industry, wherein the fluid cells may be collected through washing and centrifuging process and the fixed cells may be collected through, trypsin treatment, washing and centrifuging process.

In the above step 1, the fixation process may be conducted by formalin, Bouin's solution, Zenker solution, Susa, and Carnov's solution according to conventional methods, but is not limited in these. In an preferred example of the present invention, 13 types of gastric cancer (GC) cell lines were treated with trypsin and collected, and then a process to make them reacted and fixed in 10% neutral buffered formalin (NBF) over 24 hr was performed, wherein the NBF was exchanged to fresh NBF at every 12 hr during fixation reaction.

In the above step 2 relevant to a distinct characteristic of the present invention, medical adhesives commonly used are sufficient to use as the above medical adhesive, for instance at least one medical adhesive selected from the group comprising cyanoacrylate, fibrin glue, protein glue, polyurethane, sealant containing PEG(polyethylene glycol), and their combinations may be used, but not limited in these. In additions, for the above organic solvent, a common organic solvent is sufficient and for instance at least one organic solvent selected from the group comprising alcohol, xylene, acetone, and their combinations may be used, but not limited in these.

For the above water-soluble polymer, water-soluble polymers usually used in film formation are sufficient and for instance, at least one water-soluble polymer selected from the group comprising polyvinyl alcohol, polyethylene oxide, polyacrylamide, polyvinylpyrrolidon, polyacrylic acid, polyethyleneimine, polyamines, polyamideamine, and polydiallyl dimethylammonium chloride may be used, but not limited in these.

According to another example of the present invention, the above medical adhesive may be cyanoacrylate; the above organic solvent is acetone; and the above water-soluble polymer may be polyvinylalcohols (PVAs).

More preferably, the above cyanoacrylate may be ethyl-2-cyanoacrylate.

The polyvinylalcohols (PVAs), a synthetic polymer used in several areas such as engineering, commerce, medicine, and food, is featured by tasteless, transculent, non-toxic, white or ivory colored granular powder when it is not hydrolyzed and it shows film-forming, emulsifying, and adhesive property when it is hydrolyzed. In addition PVA has good chemical/physical stability, so shows resistance against digestion or quality deterioration which may occur during washing process and is proper to apply surface of plastic base. The method for preparing cell block can not only perform embedding easily in the process to embed the cell aggregate obtained by conventional method in paraffin by aggregating the cells using PVA, but also prepare cell block for cellular microarray over all through easy and simple processes due to good adhesiveness and water solubility of PVA.

However, because it is required to perform water soluble processes in the method for preparing cell block, there is a problem that this water-solubility of PVA may cause loss of sample. Thus in order to overcome this problem, an example of the present invention induced insolubilizing of PVA through polymerization, grafting and cross-link between PVA and cyanoacrylate by mixing and treating the cyanoacrylate to the PVA.

The cyanoacrylate is a common name of fast-acting adhesives, which has been studied and developed continuously as an industrial and household suturing tool due to its aesthetic property (transparency) and adhesive force. In late 1990's, a noble cyanoacrylate with improved adhesive force from a derivative of 2-octyl cyanoacrylate (OC) known as instant adhesive, crazy glue or super glue was developed and has been marketed and used as a wet adhesive and a wound suturing agent under approval of FDA.

The types of medical adhesives, organic solvents, and water-soluble polymers used in an preferred example of the present invention illustrate the present invention, but do not limit their types, so it is clear that any medical adhesives, organic solvents, and water-soluble polymers with similar physiochemical properties and effects to PVA, acetone, and cyanoacrylate presented concretely in the above can be substituted, mixed, and used.

It is desirable that the above organic solvent containing medical adhesive contains 0.004~0.008 wt % and the above solution containing water soluble polymer contains 3~5 wt %. The above solution containing water soluble polymer may be used as a volume of 5~10 times of the above organic solvent containing medical adhesive, but is not limited in this. According to an example of the present invention, although 1 mL of acetone containing 0.06 wt % of ethyl-2-cyanoacrylate was used as the above organic solvent containing medical adhesive and 5~10 mL of solution containing 3 wt % of PVA was used, these only illustrates the present invention and their concentration and treating amount may be adjusted properly according to types, states, and numbers of the sample cells.

In addition, the step 3) of the present invention performs the process to obtain cell block by embedding each cell aggregates obtained in the above step 2), wherein the embedding process may be performed by making paraffin, celloidin, carbowax, gelatin or synthetic resin infiltrated or freezing by conventional methods and preferably, may be performed by paraffin embedding method.

The step 4) of the present invention stamps out cell pellets from the above embedded cell block and arrays them on a fixed frame, wherein a fixed paraffin block case may be used as the above fixed frame.

The step 5) of the present invention makes the above frame where the cell pellets are arrayed to a block (solid) and a section to obtain cell block sample for cell micro array, wherein according to an preferred example of the present invention, the above solidification may be performed by microsection to 3~5 μm of thickness using a microtome (LECEA, GERMANY).

According to another example of the present invention, as results of treating acetone containing 0.006 wt % of ethyl-2-cyanoacrylate and solution containing 3 wt % of polyvinylalcohol (PVA) to the cell sediment and observing the obtained cell aggregates through SEM analysis in the process of preparing cell block of the present invention, it was found that the cells form a complex with PVA and cyanoacrylate to aggregate closely, maintaining their shapes without any damage. In addition, as results of performing cellular morphological analysis through H&E staining and molecular biological analyses such as immunohistochemistry analysis (IHC) using primary antibody specific to β-catenin and C-erb B2 protein, FISH(fluorescence in situ hybridization), and SISH(silver in situ hybridization) using probes hybridized to specific DNA sequence, it was identified that clear staining was possible by solving traditional problems such as sample loss, separation between the sample and the scaffold, and background staining as well as maintenance of cellular morphology and dense aggregation in the cell block and antigenicity to cellular protein and gene antibody and sensitivity to the gene probe were excellent.

Therefore, the present invention provides a cell block for cellular microarray prepared according to the above preparing method and because when using the cell block for cellular microarray according to the present invention, it can provide effective multiple information via excellent sensitivity to several analyses such as morphological stability, immunohistochemistry, and molecular biology even if using extremely small amount or sized fluid cells, it can be applied widely to cytological diagnosis based on cellular findings and EM study using extremely small sample.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

EXAMPLE

Example 1

Process to Prepare Paraffin Section Using the Composition for Aggregating Biological Sample According to the Present Invention In order to assist understanding on the theoretical background, the process to prepare paraffin section of the sample using the composition for aggregating biological sample is explained.

At first, centrifuge a sample fixed in formalin or alcohol (biological tissues or cells) in a centrifuge tube at 13,000rpm~15,000rpm for 1~3 min (rpm and time of centrifuge can be adjusted depending on the biological sample) and then discard the supernatant to obtain sample sediment. Prepare the first composite by mixing 1.5~2.0 part by weight of water-soluble polymer against 100 part by weight of distilled water well. Add 300~500 part by weight of the above prepared first composite to 100 part by weight of the above sample sediment.

Subsequently, prepare the second composite by adding 100 μl~200 μl of the medical adhesive to 100 mL of organic solvent and add 300~500 part by weight of the above prepared second composite to 100 part by weight of the sample sediment in the micro centrifuge tube.

When observing creation of the sediment after tapping lightly the tube for 30 sec, centrifuge the above tube at 13,000rpm~15,000rpm for 1~3 min (the rpm and time can be adjusted properly according to the sample).

After wrapping the resulting sediment with microscope lens paper, put it into a tissue capsule and soak it in alcohol for 1 hr. Repeat this process about 5 times.

Next, a paraffin block can be prepared by repeating the same process 3 times respectively for same volume of xylene and paraffin. Make the paraffin block prepared through the above process to micro-section of paraffin with 4~6 μm of thickness, using a microtome (LECEA, GERMANY).

Example 2

Function Check of the Composition for Aggregating Biological Sample of the Present Invention Using SEM and TEM In order to check how the composition for aggregating biological sample to aggregate the sample, following tests were performed.

After centrifuging lung adenocarcinoma A549 cells fixed in fixative (2% paraformaldehyde, purchased from MDPOS KOREA) with a centrifuge tube at 13,000 rpm for 1 min and then, sample sediment was obtained by discarding the supernatant.

They were postfixed with 1% $OsO_4$ dissolved in 0.1 M PB for 2 hr and dehydrated in ascending gradual series (50~100%) of ethanol. By adding 1.0 g of polyvinyl alcohol (DUSAN KOREA) to 100 mL of distilled water and mixing them well, the first composite was prepared. The prepared first composite was added as 3 times of weight against the above sample sediment in the centrifuge tube.

Subsequently, mix well 100 μl of 95% (v/v) cyanoacrylate (LOCTITE HENKEL, GERMANY) to acetone (SIGMA USA) to prepare the second composite. Add 3 times by weight of the above prepared second composite to the above centrifuge tube containing the first composite and the sample sediment. After tapping lightly the tube for 30 sec, when observing that the aggregate started to be generated, centrifuge the tube at 13,000 rpm for 3 min and obtain the sediment by discarding the supernatant. Observe and take images of the resulting sediment with SEM and TEM.

FIG. 1A~1D shows SEM images of lung adenocarcinoma A549 cells aggregated by the composition for aggregating biological sample according to an example of the present invention. Particularly, 1A indicates an assemblage formed by the composition for aggregating biological sample and lung adenocarcinoma A549 cells, 1C indicates a formation aggregated by the composition for aggregating biological sample and lung adenocarcinoma A549 cells, and 1D indicates magnified image showing the aggregated composition for aggregating biological sample and lung adenocarcinoma A549 cells.

In addition, 1E shows TEM images of lung adenocarcinoma A549 cells aggregated by the composition for aggregating biological sample according to an example of the present invention and it is identified that the composition for aggregating biological sample and the lung adenocarcinoma A549 cells are aggregated each other (in the above images, the white area indicates the composition for aggregating biological sample and the dark area is the lung adenocarcinoma A549 cells.

As shown in the above FIG. 1, it became possible to aggregate easily even cells that had been difficult to be aggregated traditionally by using the composition for aggregating biological sample according to the present invention.

Example 3

Function Check of the Composition for Aggregating Biological Sample of the Present Invention Using Ascetic Fluid of a Patient After centrifuging ascetic fluid collected from a patient with malignant tumor metastasized to the peritoneum fixed in formalin (10% neutral formalin buffer, purchased from MDPOS KOREA) with a centrifuge tube at 13,000 rpm for 1 min and then discarding supernatant, sample sediment was obtained. By adding 2.0 g of polyvinyl alcohol (DUSAN KOREA), 1.0 g of carboxymethyl cellulose, and 2.0 cc of dimethyl sulfoxide to 100 mL of distilled water and mix them well, the first composite was prepared.

Add 3 times by weight of the above prepared first composite to the above sample sediment to the centrifuge tube. Subsequently, add 100 μl of 95% (v/v) cyanoacrylate (LOCTITE HENKEL, GERMANY) and 200 μl of concentrated formalin to acetone (SIGMA USA) to prepare the second composite. Add 3 times by weight of the above prepared second composite to the above centrifuge tube containing the first composite and the sample sediment. After tapping lightly the tube for 30 sec, when observing that the aggregate started to be generated, centrifuge the tube at 13,000 rpm for 3 min and obtain the sediment by discarding the supernatant.

Wrapping the resulting sediment with microscope lens paper, it was put into a tissue capsule and then soaked in alcohol for 1 hr. This process was repeated 5 times. Next, a paraffin block was prepared by repeating the same process 3 times respectively for same volume of xylene and paraffin. The paraffin block prepared through the above process was made to micro-section of paraffin with 4 μm of thickness, using a microtome (LECEA, GERMANY).

Figure 3:
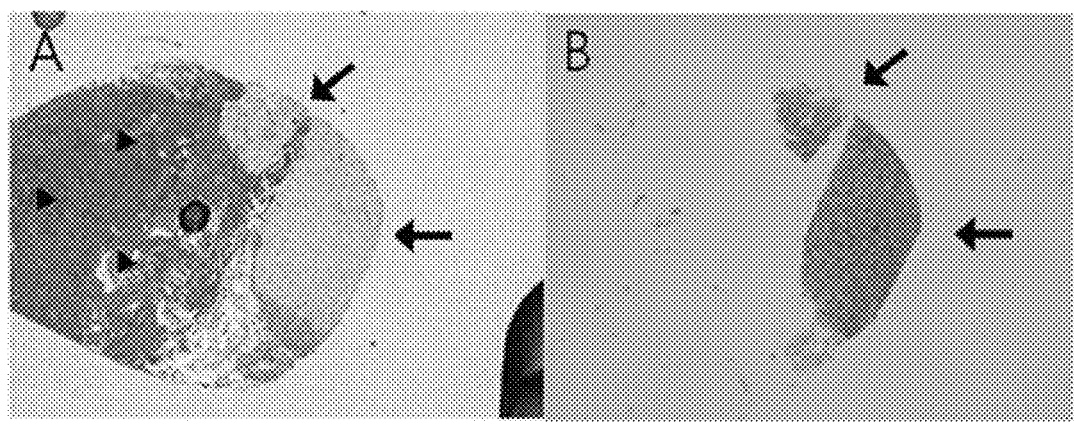
FIG. 3 are microscopic images observing paraffin sections before (A) and after eosin staining (B), which were prepared from ascitic fluid aggregated by the composition for aggregating biological sample according to an example of the present invention (the arrow indicates the sample).

FIG. 3 are microscopic images observing paraffin sections comparing before (A) and after hematoxylin and eosin staining (B) to the above prepared paraffin microsection. Particularly, FIG. 3A is an image of paraffin microsection before hematoxylin & eosin, wherein the arrow indicates the sample, 'ascetic fluid' and the head of arrow indicates the composite for aggregating biological sample of the present invention. In addition, FIG. 3B is an image of paraffin microsection, after washing it with distilled water to remove the composition for aggregating biological sample of the present invention and staining with H&E.

As shown in the above FIG. 3, it is suggested that when using the composition for aggregating biological sample of the present invention, it is possible to form an aggregate for biological fluids such as ascetic fluid. In addition, it is suggested that it is possible to stain the sample with little background staining.

Example 4

Comparison Between Conventional Methods and the Method of the Present Invention for Preparing Paraffin Block After centrifuging cells from ascetic fluid fixed in formalin (10% neutral formalin buffer, purchased from MDPOS KOREA) with a centrifuge tube at 13,000 rpm for 1 min and then discarding supernatant, sample sediment was obtained. By adding 2.0 g of polyvinyl alcohol (DUSAN KOREA) to 100 mL of distilled water and mixing them well, the first composite was prepared. The prepared first composite was added as 3 times of weight against the above sample sediment.

Subsequently, mix well 100 μl of 95% (v/v) cyanoacrylate (LOCTITE HENKEL, GERMANY) to acetone (SIGMA USA) to prepare the second composite. Add 3 times by weight of the above prepared second composite to the above centrifuge tube containing the first composite and the sample sediment. After tapping lightly the tube for 30 sec, when observing that the aggregate started to be generated, centrifuge the tube at 13,000 rpm for 3 min and obtain the sediment by discarding the supernatant. Wrapping the resulting sediment with microscope lens paper, it was put into a tissue capsule and then soaked in alcohol for 1 hr. This process was repeated 5 times.

Next, a paraffin block was prepared by repeating the same process 3 times respectively for same volume of xylene and paraffin. The paraffin block prepared through the above process was made to micro-section of paraffin with 4 μm of thickness, using a microtome (LECEA, GERMANY).

Figure 4:
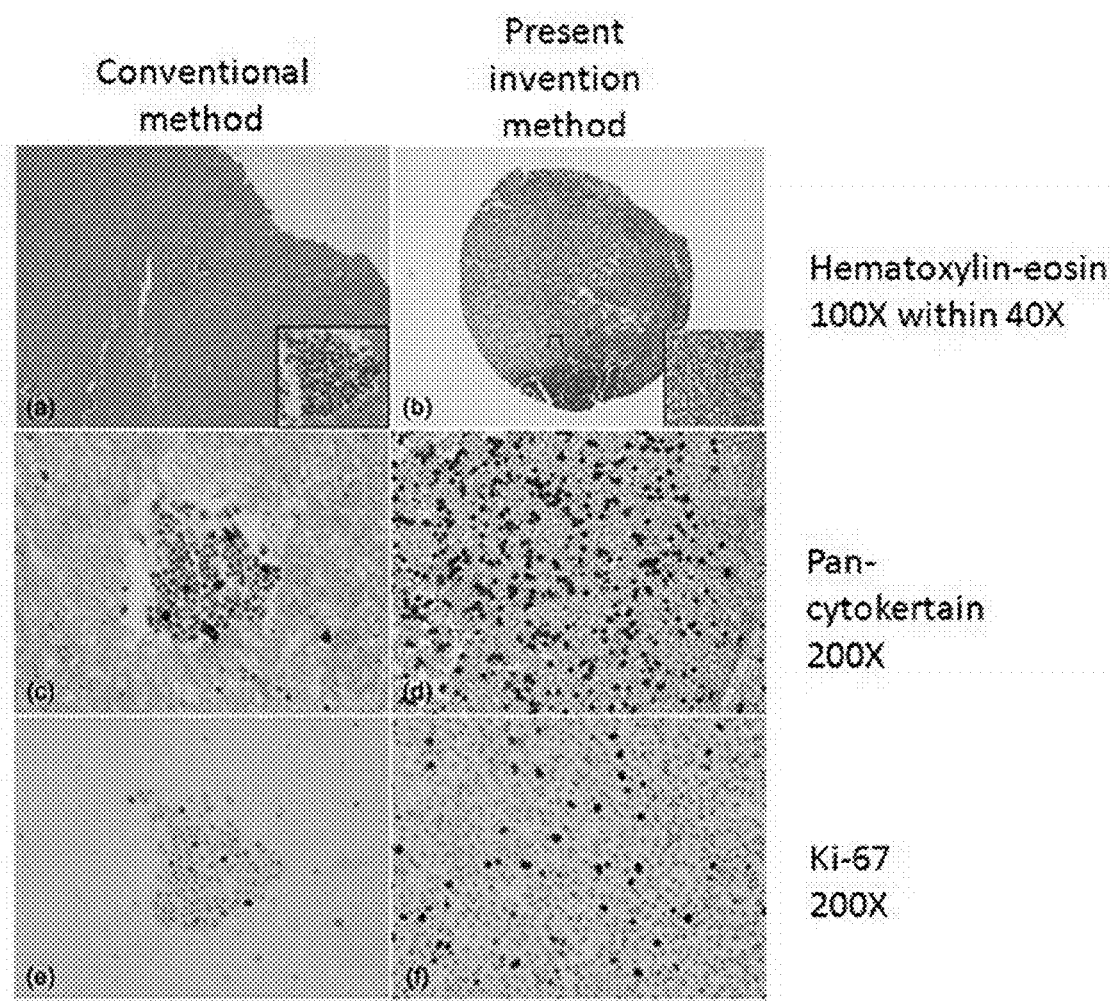
FIG. 4 are microscopic images observing paraffin sections after performing hematoxylin & eosin staining (H&E staining), Pan cytokeratin immunostaining, and Ki-67 immunostaining, which were prepared from ascitic fluid according to the conventional method for preparing cell block and the present invention.

FIG. 4 are microscopic images observing the above prepared paraffin micro-sections at 40 (a, b) and 200 (c~f)) magnifications respectively, which were stained with hematoxylin and eosin staining (a, b), pancytokeratin immunostaining (c, d) and Ki-67 immunostaining (e, f) (the images inserted into the drawings was 100 magnifications).

In the above FIG. 4, the images on the right (b,d,f) are images of paraffin section prepared by the noble method for preparing paraffin block of the present invention and the images on the left (a, c, e) are images of paraffin section prepared by the conventional method. It is found that the sample of image on the right panel is further smaller, denser, and easier to observe due to little background staining than the sample of image on the left panel. Namely, it is suggested that the paraffin micro-section prepared according to the present invention has much less of sample loss, much less of background staining, and higher resolution.

Example 5

Observation of Ascetic Fluid from a Patient with Malignant Tumor Metastasized to the Peritoneum According to the Present Invention Ascetic fluid of a patient with malignant tumor metastasized to the peritoneum was collected, prepared to paraffin block by the method same to the above Example 4 and observed.

FIG. 5A~5D are microscopic images observing paraffin sections after performing hematoxylin & eosin staining (H&E staining) (5A), vimentin immunohistochemical staining (5B), Pan cytokeratin immunostaining (5C), and PAS histochemical staining (5D), which were prepared from ascetic fluid of a patient with malignant tumor metastasized the peritoneum according to the conventional method for preparing cell block and the present invention.

As shown in the above FIG. 5A~5D, it is suggested that the method for preparing paraffin block can result in higher quality of staining to perform histochemical analysis and immunohistochemical analysis compared to the conventional paraffin block preparing methods. In addition, it is suggested that it is possible to prepare paraffin block with minimized sample loss, no background staining, and higher resolution according to the present invention.

Example 6

Observation of Pancreatic Cancer Cells According to the Present Invention

After collecting tumor cells from a patient with pancreatic cancer, fixing them in formalin (10% neutral formalin buffer, purchased from MDPOS KOREA), and centrifuging them in a centrifuge tube at 13,000 rpm for 1 min, sample sediment was obtained by discarding supernatant. By adding 1.0 g of polyvinyl alcohol and 1.0 g of polyethylene oxide to 100 mL of distilled water and mixing them well, the first composite was prepared. The prepared first composite was added as 3 times of weight to the centrifuge tube containing the above sample sediment.

Subsequently, mix well 100 μl of 95% (v/v) cyanoacrylate (LOCTITE HENKEL, GERMANY) to acetone (SIGMA USA) to prepare the second composite. Add 3 times by weight of the above prepared second composite to the above sample sediment in the centrifuge tube.

After tapping lightly the tube for 30 sec, when observing that the aggregate started to be generated, centrifuge the tube at 13,000 rpm for 3 min and obtain the sediment by discarding the supernatant. Wrapping the resulting sediment with microscope lens paper, it was put into a tissue capsule and then soaked in alcohol for 1 hr. This process was repeated 5 times.

Next, a paraffin block was prepared by repeating the same process 3 times respectively for same volume of xylene and paraffin. The paraffin block prepared through the above process was made to micro-section of paraffin with 4 μm of thickness, using a microtome (LECEA, GERMANY).

Figure 6:
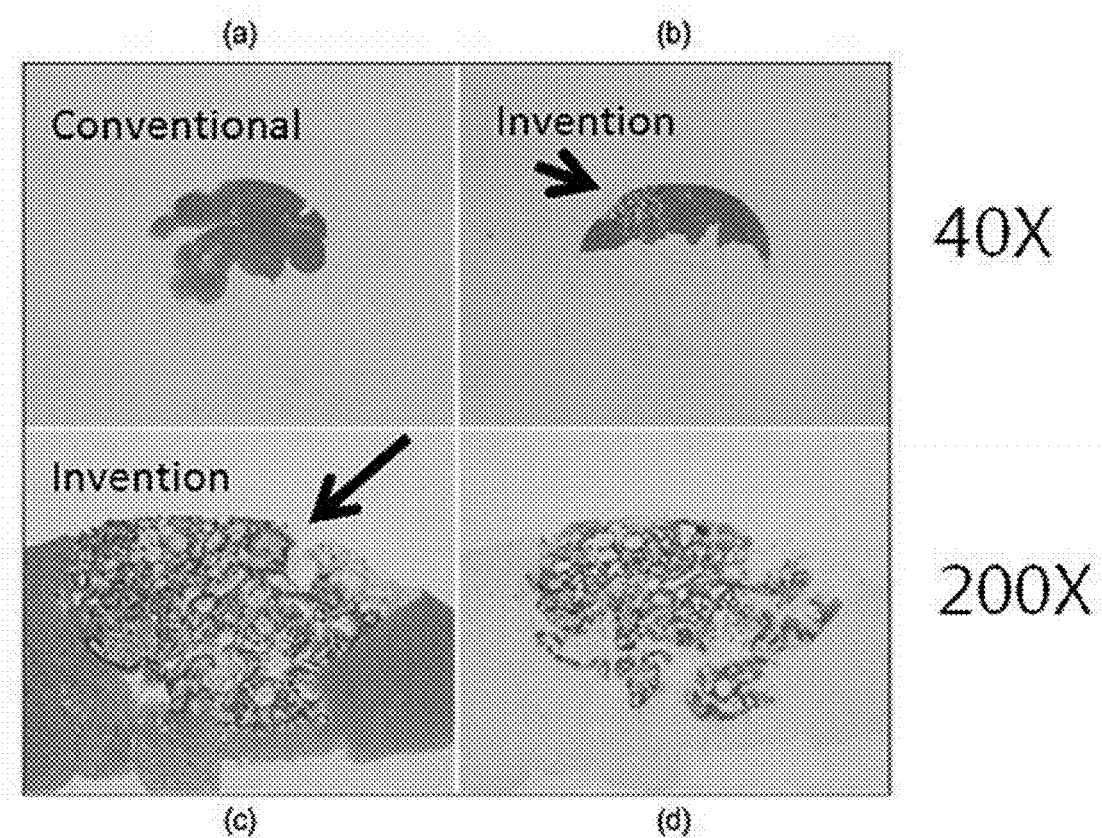
FIG. 6 are microscopic images observing paraffin sections after performing E-cadherin immunostaining, which were prepared from pancreatic cancer cells according to the conventional method for preparing cell block and the present invention.

FIG. 6 are microscopic images observing paraffin microsections after E-cadherin immunostaining of the paraffin block prepared by conventional methods and the method of the present invention at 40× magnification (FIG. 6(a), FIG. 6(b)) and 200× magnifications (FIG. 6(c), FIG. 6(d)). FIG.

6(a) was an image of paraffin micro-section prepared by conventional method for preparing cell block, which failed to identify the pancreatic cancer cells. On the contrary, FIGS. 6(b) and 6(c) were images of paraffin microsection prepared by the method of present invention, which showed the pancreatic tumor cells clearly. In the FIGS. 6(b) and 6(c), the arrow indicates the pancreatic tumor cells. Therefore from the above results, it was suggested that similar to the Example 1, it was possible to prepare paraffin block resulting in minimal loss of sample, no background staining, and higher resolution.

Example 7

Observation of Cerebrospinal Fluid of a Patient with Lung Cancer

After centrifuging cerebrospinal fluid (CSF) of a patient with lung cancer fixed in formalin (10% neutral formalin buffer, purchased from MDPOS KOREA) with a centrifuge tube at 13,000 rpm for 1 min and then discarding supernatant, sample sediment was obtained. By adding 2.0 g of polyvinyl alcohol (DUSAN KOREA), 1.0 g of carboxymethyl cellulose, and 2.0 g of demethyl sulfoxide to 100 mL of distilled water and mix them well, the first composite was prepared. Add 3 times by weight of the above prepared first composite to the above sample sediment to the centrifuge tube.

Subsequently, add 100 µl of 95% (v/v) cyanoacrylate (LOCTITE HENKEL, GERMANY) and 200 µl of concentrated formalin to acetone (SIGMA USA) to prepare the second composite. Add 3 times by weight of the above prepared second composite to the above sample sediment in the centrifuge tube. After tapping lightly the above tube for 30 sec, when observing that the aggregate started to be generated, centrifuge the tube at 13,000 rpm for 3 min and obtain the sediment by discarding the supernatant.

Wrapping the resulting sediment with microscope lens paper, it was put into a tissue capsule and then soaked in alcohol for 1 hr. This process was repeated 5 times. Next, a paraffin block was prepared by repeating the same process 3 times respectively for same volume of xylene and paraffin. The paraffin block prepared through the above process was made to micro-section of paraffin with 4 µm of thickness, using a microtome (LECEA, GERMANY).

Figure 7:
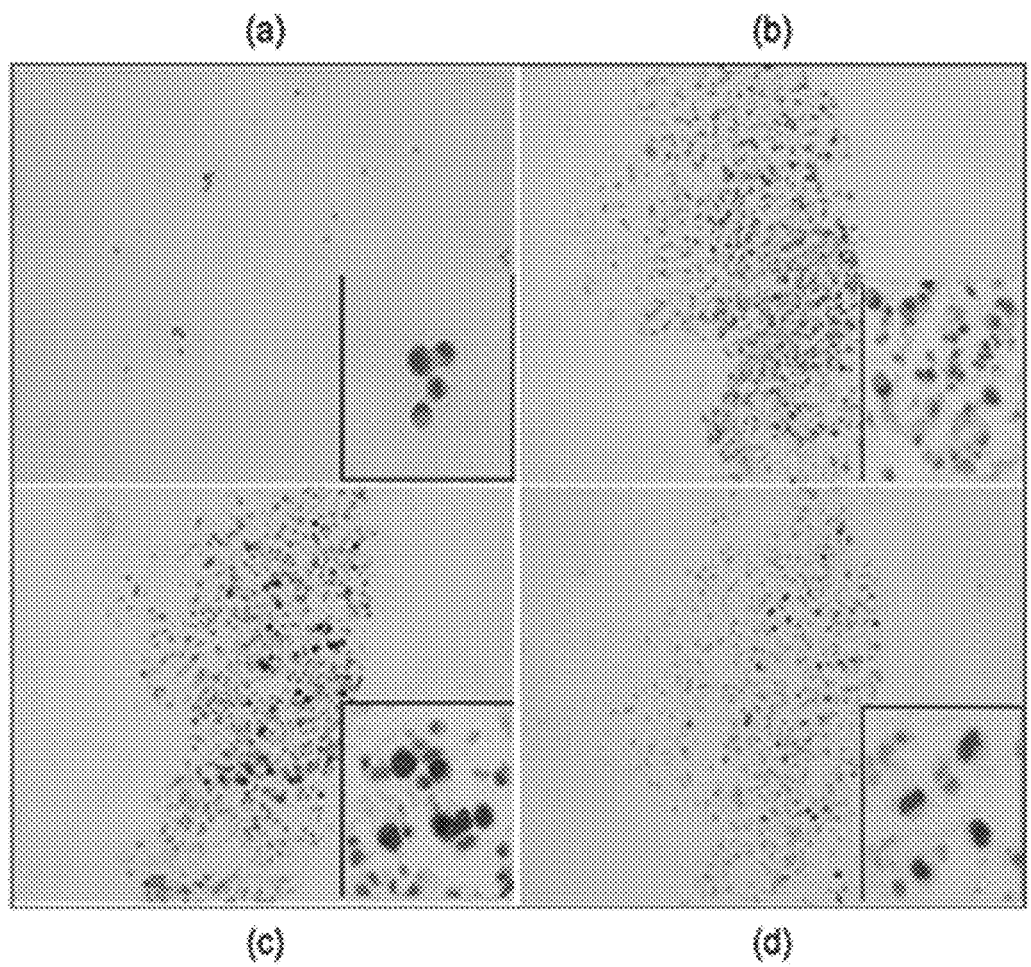
FIG. 7 are microscopic images observing paraffin sections at 100 and 400 magnifications, which were prepared from cerebrospinal fluid of a patient with lung cancer according to the conventional method for preparing cell block and the present invention.

FIG. 7(a) shows PAP smear performed specimen other than the method for paraffin block of the present invention, where it was found that the density of atypical cells was very low and it failed to identify the desired cells. On the contrary, FIG. 7(b) performing H&E staining for the paraffin section prepared by the present invention, FIG. 7(c) performing Cytokeratin-5 staining, and FIG. 7(d) performing TFF staining to the paraffin section prepared by the present invention show multiple atypical cells clearly (the magnification of image inserted into the drawing was 400×). Therefore, it is suggested that the paraffin micro-section prepared according to the present invention has much less of sample loss, much less of background staining, and higher resolution.

Example 8

Observation of Whole Blood Buffy Coat from a Patient with Breast Cancer According to the Present Invention Whole blood buffy coat collected from a patient with breast cancer was prepared to paraffin block and observed.

Figure 8:
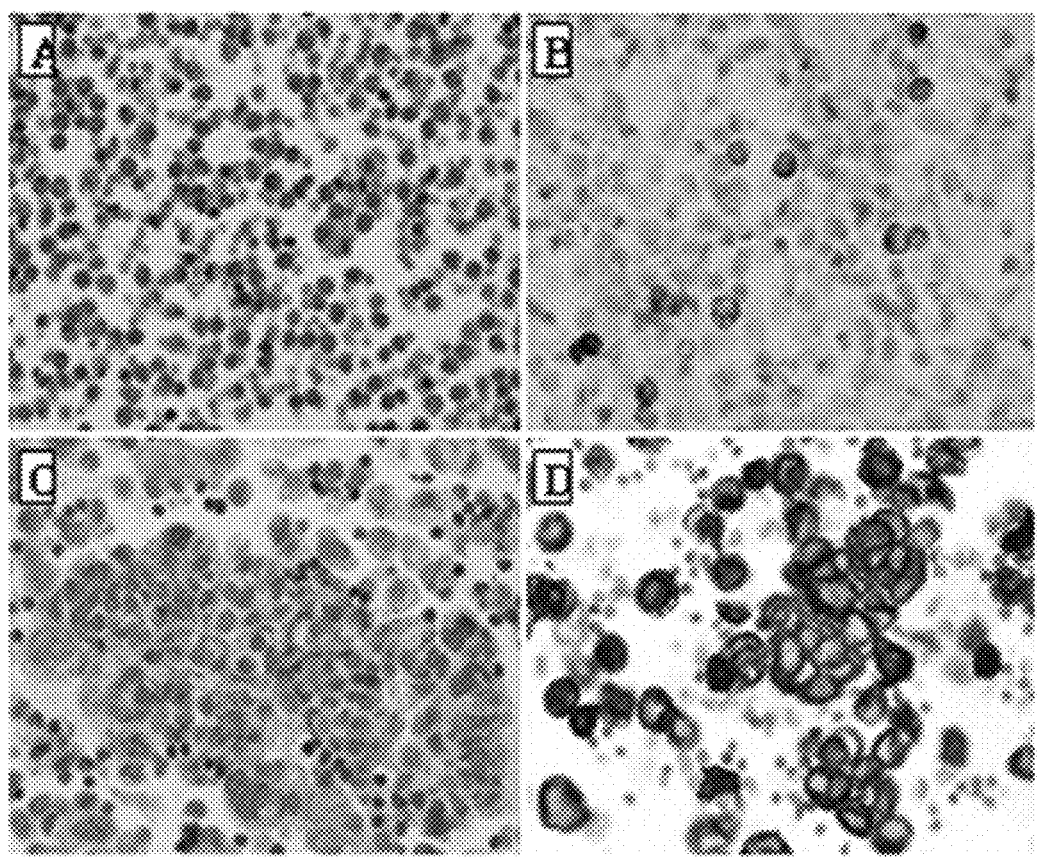
FIG. 8 are microscopic images observing paraffin sections after performing hematoxylin & eosin staining (H&E staining), CD3 immunohistochemical staining, PAS immunohistochemical staining, and pan cytokeratin immunohistochemical staining, which were prepared from whole blood buffy coat according to another example of the present invention.

FIG. 8A~5D are microscopic images observing paraffin sections after performing hematoxylin & eosin staining (H&E staining) (FIG. 8A), CD3 immunohistochemical staining (FIG. 8B), PAS immunohistochemical (FIG. 8C), and pan-cytokeratin immunohistochemical staining (FIG. 8D), which were prepared from ascetic fluid of a patient with malignant tumor metastasized the peritoneum according to the conventional method for preparing cell block and the present invention.

As shown in the above FIG. 8A~5D similar to the Example 4, it is suggested that it is possible to confirm the whole buffy coat that had not seen at all by the traditional cell block preparing methods and prepare paraffin section with no background staining and higher resolution.

Example 9

Availability of the Present Invention for In Vitro and In Vivo Cells

In order to determine if the method for preparing paraffin block of the present invention can be applied to in vitro cultured and in vivo collected cells, mouse adenocarcinoma cells collected from mice (MC 38 mouse colon adenocarcinoma cell line) and in vitro cultured MCF cell line were prepared to paraffin block and observed by the same method to the Example 4.

Figure 9:
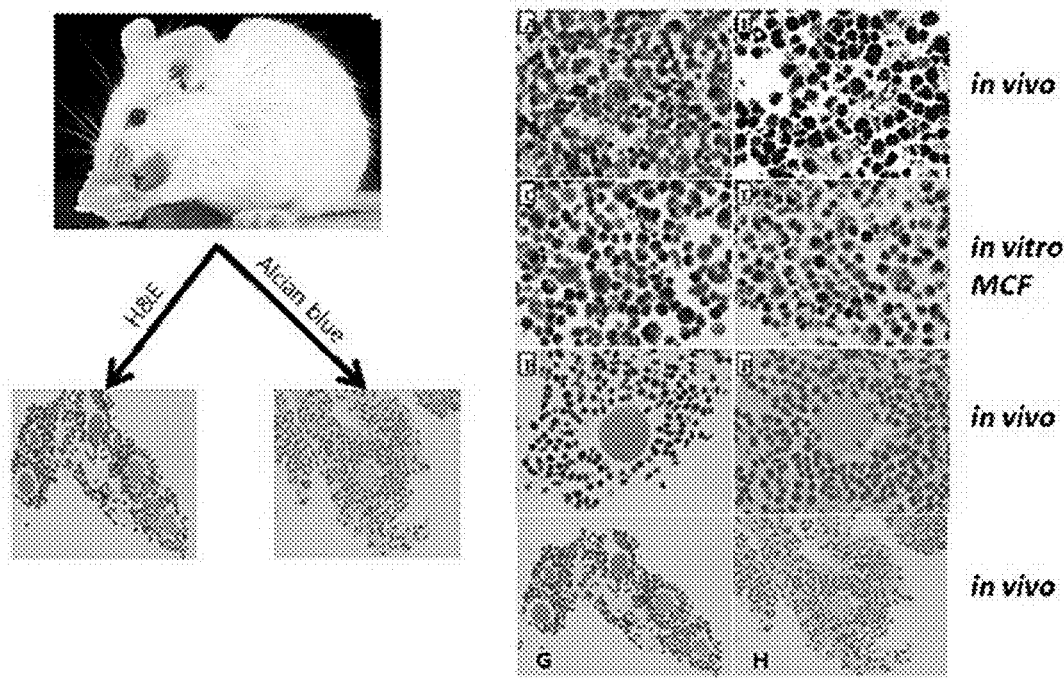
FIG. 9 are microscopic images observing paraffin sections after performing H&E staining and PCNA immunohistochemical staining, which were prepared from MC 38 mouse colon adenocarcinoma cell line and MCF cell line according to another example of the present invention.

FIGS. 9A and 9B are microscopic images of paraffin section prepared by using MC 38 mouse colon adenocarcinoma cell line at 400× magnification after H&E staining (FIG. 9A) and PCNA immunohistochemical staining (9B). In addition, FIGS. 9C and 9D are microscopic images of paraffin section prepared by using in vitro cultured MCF cell line at 400× magnification after H&E staining (FIG. 9C) and Tubulin staining (FIG. 9D).

As shown in the FIG. 9A~9D, it was found that when using the method for preparing paraffin block according to the present invention, both in vivo collected and in vitro cultured sample could show clear cells and their cytoplasm and dense aggregation of the cells.

Additionally, ovarian sample collected from a mouse were prepared to a paraffin block and observed by the same method to Example 7. FIG. 9E and FIG. 9F are microscopic images of paraffin block prepared by using ovarian samples collected from a mouse respectively at 100× magnification after H&E staining (FIG. 9E) and alcian blue staining (FIG. 9F) and FIG. 9G and FIG. 9H are microscopic images of the same at 10× magnification.

As shown in the above FIG. 9E~9H, it is suggested that it is possible to prepare a paraffin section having minimized sample loss, no background staining, and higher resolution.

Example 10

Observation of Ductal Adenocarcinoma Cells According to the Present Invention

Ductal adenocarcinoma was collected from a patient with ductal adenocarcinoma using EUS-fine needle aspiration, prepared to paraffin block by the same method to Example 4 and observed.

Figure 10:
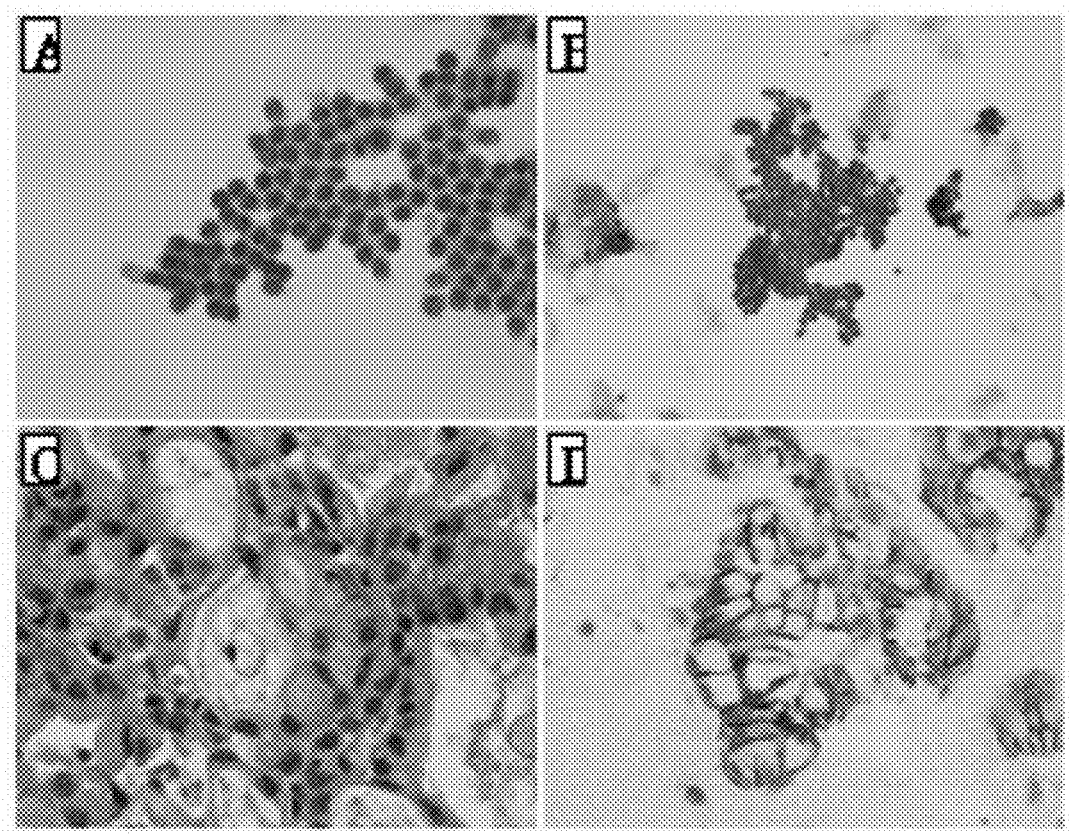
FIG. 10 are microscopic images observing paraffin sections after performing H&E staining, PAP immunohistochemical staining, and E-cadherin immunohistochemical staining, which were prepared from pancreatic ductal adenocarcinoma cells of a patient with pancreatic ductal adenocarcinoma according to another example of the present invention.

FIGS. 10A, 10B, and 10D are microscopic images of paraffin section prepared by an example of the present invention using ductal adenocarcinoma cells after H&E staining (FIG. 10A), PAP immunohistochemical staining (FIG. 10B) and E-cadherin immunohistochemical staining (FIG. 10D) and FIG. 10C is a magnified image of FIG. 10A.

As shown in the above FIG. 10A~10D, it is suggested that it is possible to confirm the ductal adenocarcinoma that had not seen at all by the traditional fine needle aspiration cytology and prepare observable paraffin section with no background staining and higher resolution.

Example 11

Performance Check Up of the Method for Preparing Paraffin Block According to the Present Invention Using Lung Adenocarcinoma In order to check up performance of the method for preparing paraffin block with biological sample, at first a paraffin block was prepared by the same method to the Example 4 using lung adenocarcinoma.

Figure 11:
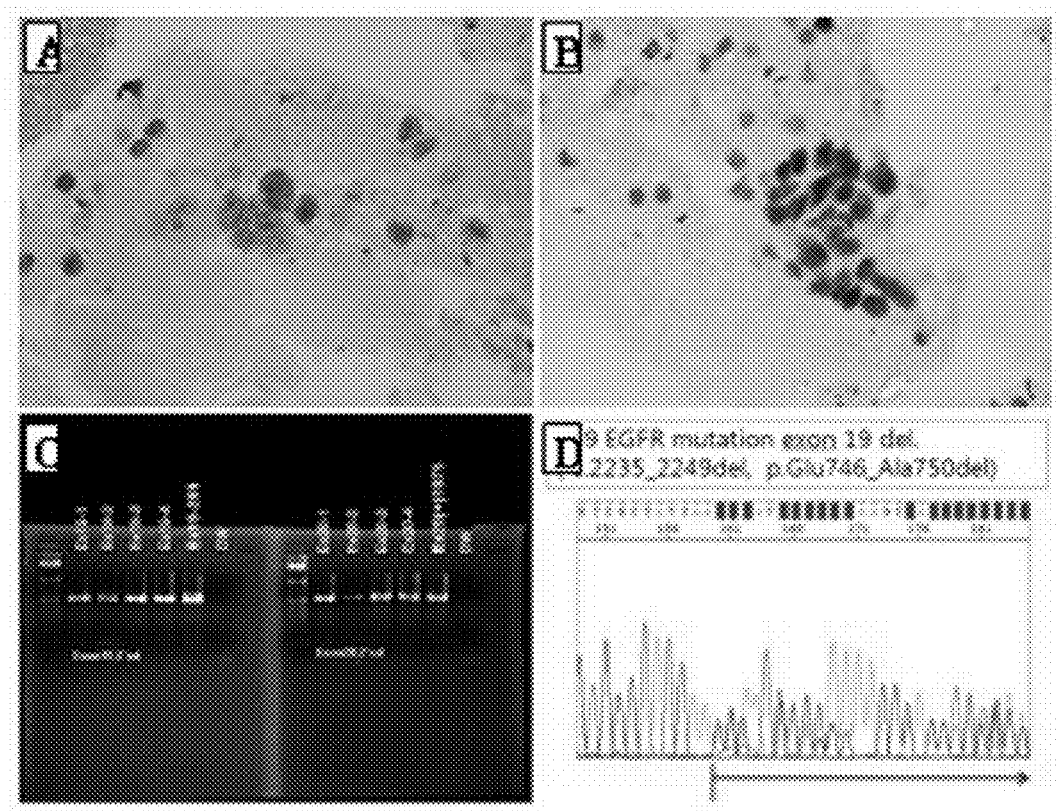
FIG. 11 are DNA images that isolate DNA from paraffin section prepared from lung adenocarcinoma cells and determine integrity of the isolated DNA.

FIG. 11A is a microscopic image of paraffin block prepared by the method for preparing for paraffin block of the present invention after H&E staining, FIG. 11B is an image after TTF-1 immunohistochemical staining, FIG. 11C is a result of DNA electrophoresis isolated from the above paraffin block, and FIG. 11D is a histogram showing results of Epidermal growth factor receptor (EGFR) mutagenesis on the above isolated DNA.

As shown in the above FIG. 11A~11D, it is identified that the method for preparing paraffin block according to the present invention can preserve the sample to be embedded in the paraffin block completely including their shape and molecular properties even as well as DNA of the sample.

Example 12

Comparison of Paraffin Block Preparation Method Between Smear Slide Method and the Present Invention In order to compare the paraffin block preparation method between the traditional smear slide method and the present invention using needle aspiration biopsy of human neck mass, following experiments was done.

At first, sample was collected and prepared to a slide from human neck mass using the needle aspiration biopsy. Next, after preparing the sample to paraffin block by the same method to the Example 4, H&F staining and AFB staining were performed.

Figure 12:
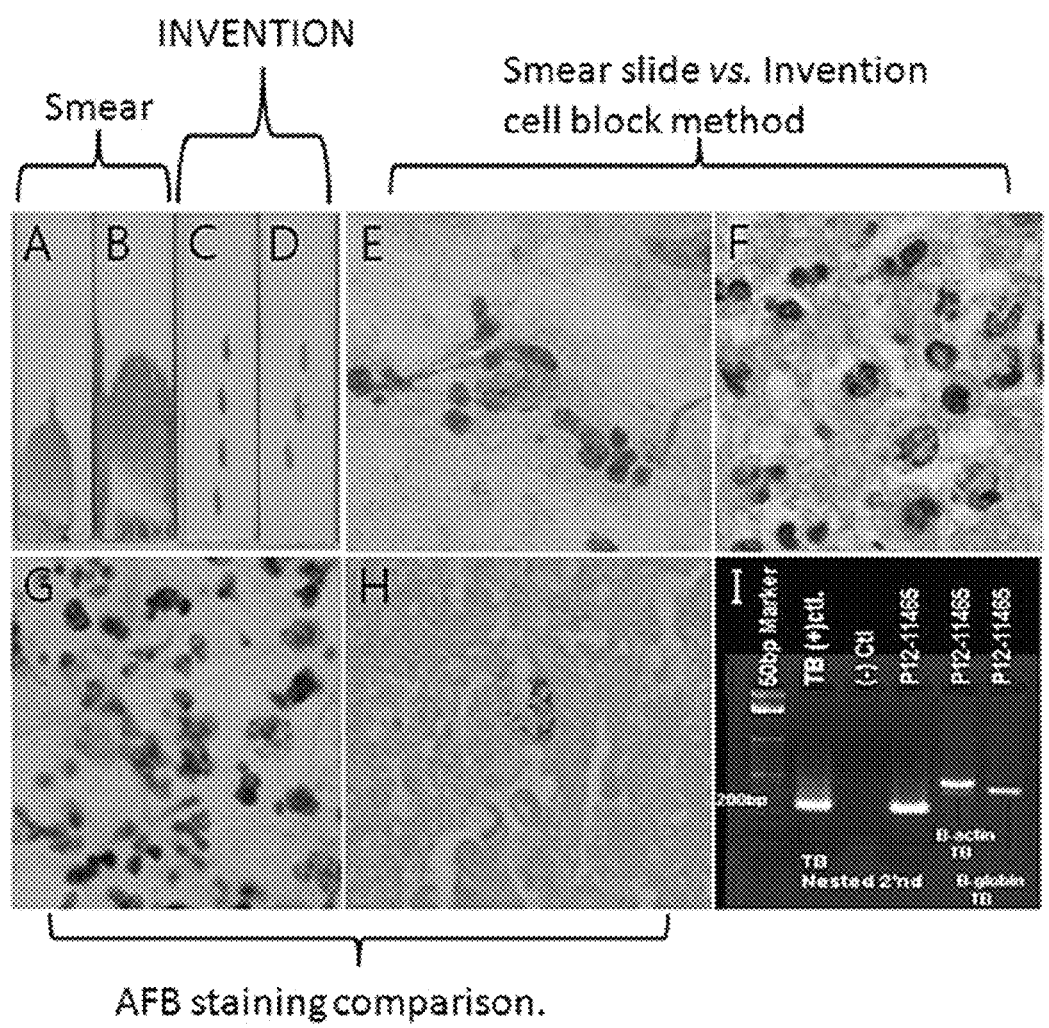
FIG. 12 are microscopic images observing paraffin sections after performing H&E staining and AFB staining, which were prepared from human neck mass obtained by fine needle aspiration biopsy according to the conventional smear slide method and another example of the present invention.

FIG. 12A and FIG. 12B are results of H&F staining and AFB staining on the slide prepared by smear slide method; FIGS. 12C and 12D are results of H&F staining and AFB staining on the paraffin block prepared according to the present invention; FIG. 12E is a magnified microscopic image of slide prepared by smear slide method at 1000× magnification after H&F staining; and FIG. 12F is a microscopic image of paraffin block prepared according to the present invention at 1000× magnification after H&F staining. In addition, FIG. 12G is a magnified microscopic image of slide prepared by smear slide method at 1000× magnification after AFB staining, FIG. 12H is a microscopic image of paraffin block prepared according to the present invention at 1000× magnification after AFB staining, and FIG. 12I is a image of DNA electrophoresis extracted from the paraffin block prepared by the present invention.

The smear slide method is a test method that has been performed in the cytology field for long time, which is used for early cancer examination or specific material test. However, although this method is easy and useful, because it is not a method to prepare a paraffin block it has a detection limit to extremely small amount or small sized sample.

As shown in FIG. 12A~12D, it is found that while the traditional smear slide cannot detect target cells from the human neck mass because of strong spreading, the paraffin block prepared by the present invention has clear resolution and can detect target cells from the human neck mass.

In addition, as shown in FIG. 12E~FIG. 12H, it is found that while the traditional smear slide cannot detect apparent shape of cells in spite of H&F or AFB staining, the paraffin block prepared by the present invention can show apparent shape of cells in H&F or AFB staining. Therefore, it is identified that the paraffin block preparing method of the present invention can detect desired cells that had not been detected by traditional method and facilitate detection of them.

Example 13

Comparison of Paraffin Block Preparing Method Between Traditional AGFT Cell Block and the Present Invention In order to compare the paraffin block preparing method between traditional AFGT cell block method and the present invention, following experiments were conducted.

At first, collect samples from the thyroid gland using fine-needle aspiration biopsy, prepare a cell block with the AGAR cell block method, and then perform H&F or PAP staining to it. Next, after preparing the sample to paraffin block by the same method to the Example 4, H&F staining and PAP staining were performed.

Figure 13:
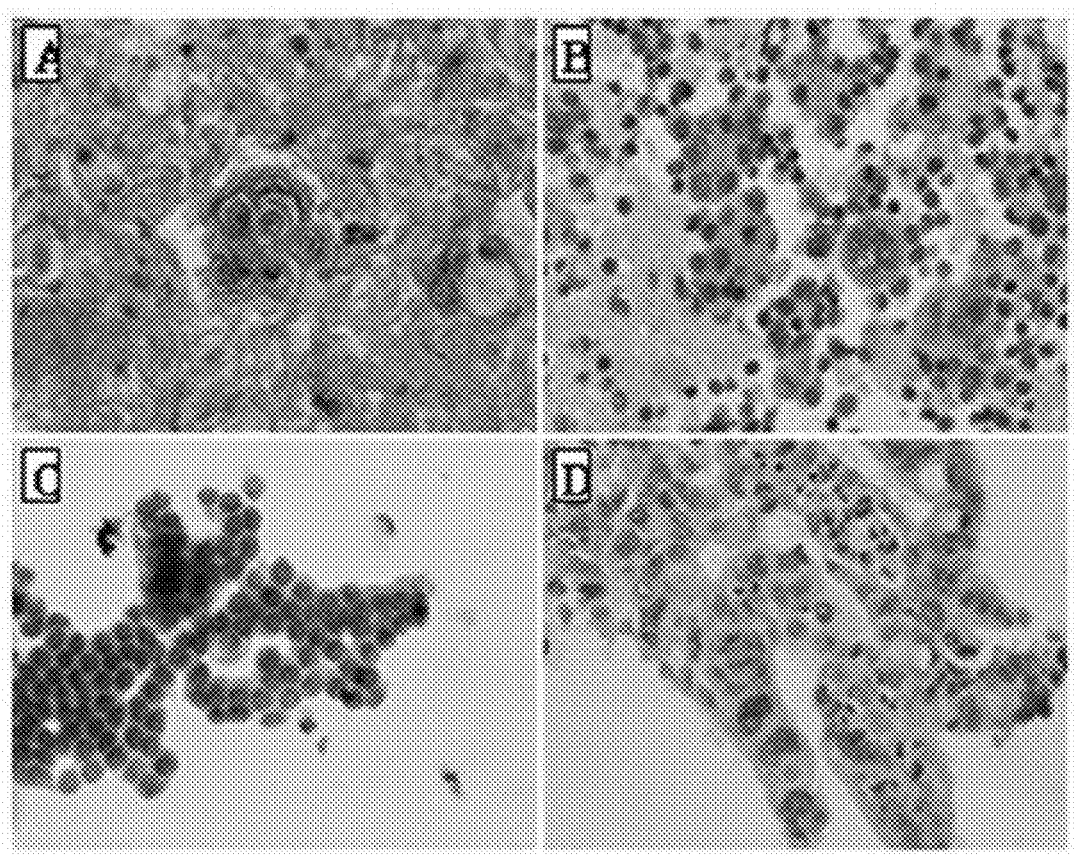
FIG. 13 are microscopic images observing paraffin sections after performing H&E staining and PAP staining, which were prepared from thyroid sample obtained by fine needle aspiration biopsy according to the conventional AGAR cell block method and another example of the present invention.

FIGS. 13A and 13C are result images of thyroid gland cell block prepared by the AGAR cell block method and stained with H&F and PAP staining, and FIGS. 13B and 13D are result images of thyroid gland cell block prepared by the present invention and stained with H&F and PAP staining.

As shown in FIG. 13A~13D, it is identified that the paraffin block preparing method according to the present invention has almost no background staining and higher resolution compared with the traditional AGAR cell block. Therefore, the present invention can detect even fine cells that had not been detected with the traditional method.

Example 14

Preparation of Cell Block for Cellular Microarray According to the Present Invention Cell block preparation for cellular microarray against 13 types of gastric cancer (GC) cell line including AGS, IM95M, MKN-1, MKN-28, MKN-45, MKN-74, N87, NCC-19, NCC-20, NCC-24, NCC-59, NUGC-3, and NUGC-4 was performed and each process of them was illustrated briefly in FIG. 14.

After suspending and collecting each cell through conventional trypsin treatment, each cell number was determined and cell pellets were obtained by centrifuging. After re-suspending the above cell pellets by adding 1.5 mL of neutral buffered formalin (NBF) (MDPOS KOREA) and making it react for over 24 hr (exchange with fresh NBF after 12 hr of resuspending), centrifuge them at 10,000 rpm for 5 min and discard supernatant (Step 1 in FIG. 14).

After residual NBF completely by using Whatman filter paper, add 1 mL of acetone containing 0.006 wt % of ethyl-2-cyanoacrylate and 5 mL of solution containing 3 wt % of PVA to the cell pellet, make them react each other for 10 min, and obtain cell aggregates by centrifuging them at 10,000 rpm for 5 min (Step 2 in FIG. 14).

After wrapping the obtained each cell aggregate with microscope lens paper, perform paraffin infiltration to embed them, stamp out the embedded cell pellets with a 2-3 mm sized sharp skin puncher, and array them on a fixed paraffin block case (Step 3 and 4 in FIG. 14).

After making them paraffin block again, perform sectioning of them to 5 μm thickness by using a microtome (LECEA, GERMANY) to prepared the cell block for cellular microarray according to the present invention (Step 5 in FIG. 14).

Test Example

Cellular Microarray Analysis

Against the cell block for cellular microarray prepared in the above Example 14, morphological, histochemical, immunohistochemical, and molecular biological studies such as FISH (fluorescence in situ hybridization) and SISH (silver in situ hybridization) were performed.

1) Confirmation of Cell Aggregate—SEM Analysis

Against A549 Adenocarcinoma cell aggregate obtained by treating acetone containing 0.006 wt % of ethyl-2-cyanoacrylate and solution containing 3 wt % of PVA according to the above preparation example, SEM (scanning electron microscopy) analysis was performed with SEM (FE SEM S-800, Hitachi, Japan).

Figure 15:
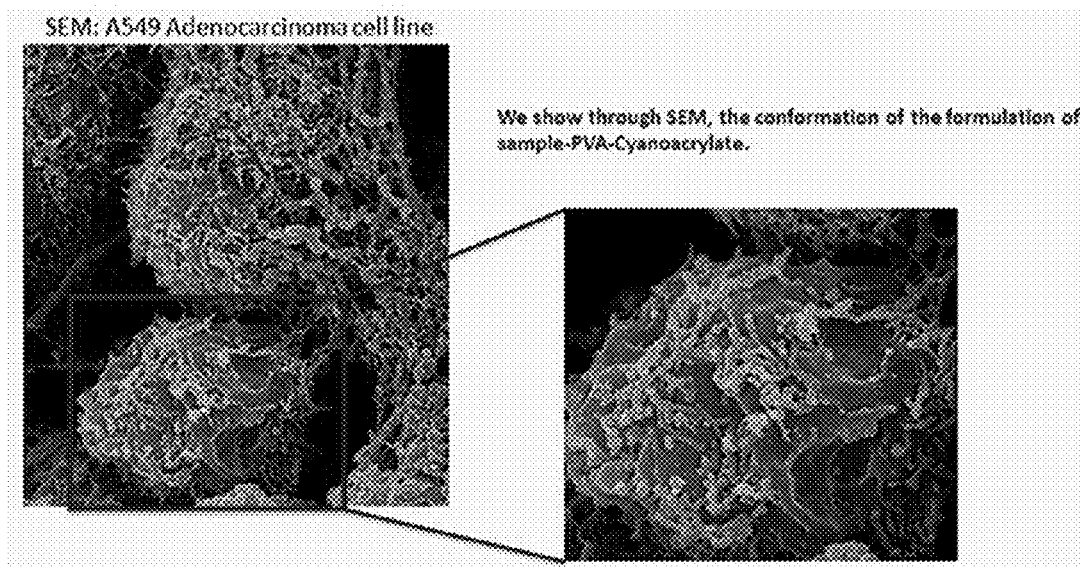
FIG. 15 is SEM (scanning electron microscopy) analysis images on adenocarcinoma according to another example of the present invention, which were obtained from an acetone containing ethyl-2-cyanoacrylate and an water-soluble solution containing polyvinylalcohol (PVA) according to another example of the present invention.

As results of this as shown in FIG. 15, it was identified that the cells formed a complex with PVA and cyanoacrylate and was aggregated densely, maintaining their shape without damage.

2) Morphological Analysis—Confirmation through H&E Staining and Immunohistochemical (IHC) Analysis Against the cell block prepared in the above Example 14, cell morphology analysis was performed through Hematoxylin and Eosin (H&E) staining and immunohistochemistry (IHC) with primary antibody specific to C-erb B2.

For H&E staining, treat 5% dehydrated ethanol containing 0.5% Harris hematoxylin (Merck), 10% aluminum potassium sulfate (Sigma), and 0.25% mercury (II) oxide red (Aldrich) to the cell block sample, incubate them for 3 min, rinse them with water, wash them after agitation for 1 min, make them pass through 70% alcohol containing 0.1% HCl rapidly, wash them with water for 1 min, and then rinse them with water after soaking into deionized water containing 0.1% $NH_4OH$ 5 times. Then, incubate the above sample in 60% acidic alcohol containing 0.25% Eosin Y (Sigma) for 15 sec, rinse it with water, and then dehydrate it through 3 times of treatment with each of 70% ethanol and 90% ethanol 3 times of treatment with 100% ethanol. After treating the dehydrated sample in xylene bath 3 times, perform mounting using Canada balsam (Merck).

In order to perform IHC analysis using a primary antibody specific to C-erb B2 protein, deparaffinize the cell block prepared in the above preparation example and make it react with microwave in 10 mM sodium citrate buffer (pH 6.0) for 30 min to recover its antigenicity. Then treat the sample with 1:100 diluted anti-C-erb B2 monoclonal antibody (DAKO Corporation, Carpinteria, Calif.), incubate them at 4° C. for 12 hr, and then induce colorimetric reaction through EnVision theough with Poly-HRP(DAKO Corporation, Carpinteria, Calif.).

Figure 16:
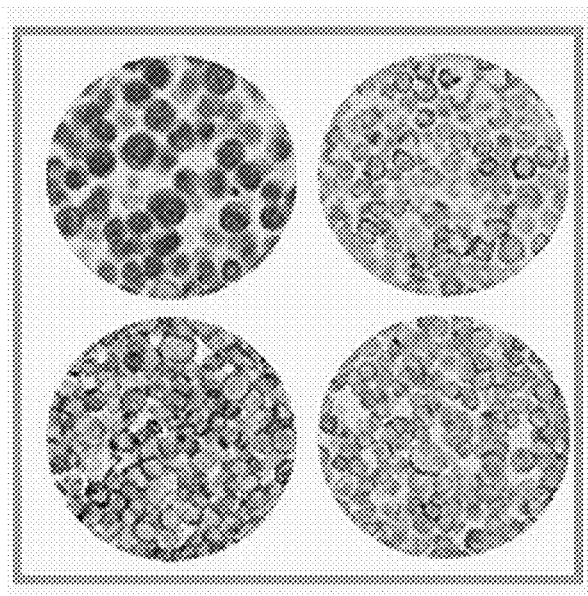
FIG. 16 are result images of immunohistochemistry (IHC) after performing H&E staining (left on the top) and C-erb B2 protein specific primary antibody to cell block specimen for cellular microarray according to another example of the present invention.

As the result as shown in FIG. 16, it was identified that preparing cell block according to the present invention could be applied usefully to morphological and histochemical analysis by making the cells maintain their shape and aggregated densely and minimize the sample loss. In addition, it was identified also that there was almost no background staining had induced some problems in traditional preparing methods, so it was possible to obtain clear analysis results.

3) Immunohistochemical Analysis—Confirmation of Antigenicity Against Anti β-catenin and Anti C-erb B2 Antibody Against the cell block prepared in the above preparation example, IHC analysis was performed by treating anti β-catenin monoclonal antibody (Transduction Laboratories, Lexington, Ky.) and anti C-erb B2 monoclonal antibody (DAKO Corporation, Carpinteria, Calif.) at 1:250 and 1:100 of dilution ratio respectively according to conventional method and antigenicity degree (IHC grade) of cells to each antibody was determined, evaluated, and described in below Table 1.

TABLE 1

| Gastric Cancer Cell Line | β-catenin | C-erb B2 |
|---|---|---|
| AGS | +3 | — |
| IM95M | +2 | +2 |
| MKN-1 | — | — |
| MKN-28 | +2 | — |
| MKN-45 | +2 | — |
| MKN-74 | +2 | — |
| N87 | — | +3 |
| NCC-19 | — | +1 |
| NCC-20 | +2 | +1 |
| NCC-24 | +3 | — |
| NCC-59 | +3 | — |
| NUGC-3 | +1 | — |
| NUGC-4 | — | +2 |

Figure 17:
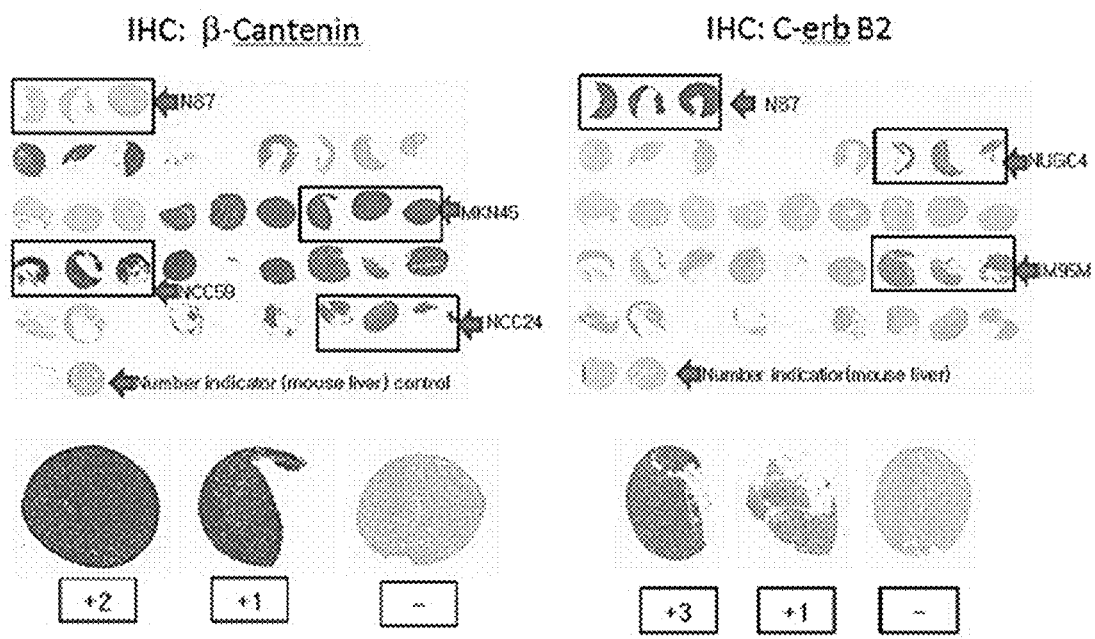
FIG. 17 are result images of histochemical assay and immunohistochemistry (IHC) after performing β-catenin and C-erb B2 protein specific primary antibody to cell block sample for cellular microarray according to another example of the present invention.

As the results as shown in the above Table 1 and FIG. 17, it was identified that when performing IHC analysis using the cell block for cellular microarray prepared by the present invention, it was possible to clear analysis results by maintaining its antigenicity and sensitivity of this analysis was excellent as much able to discriminate protein expression of each cell with naked eyes.

Figure 5:
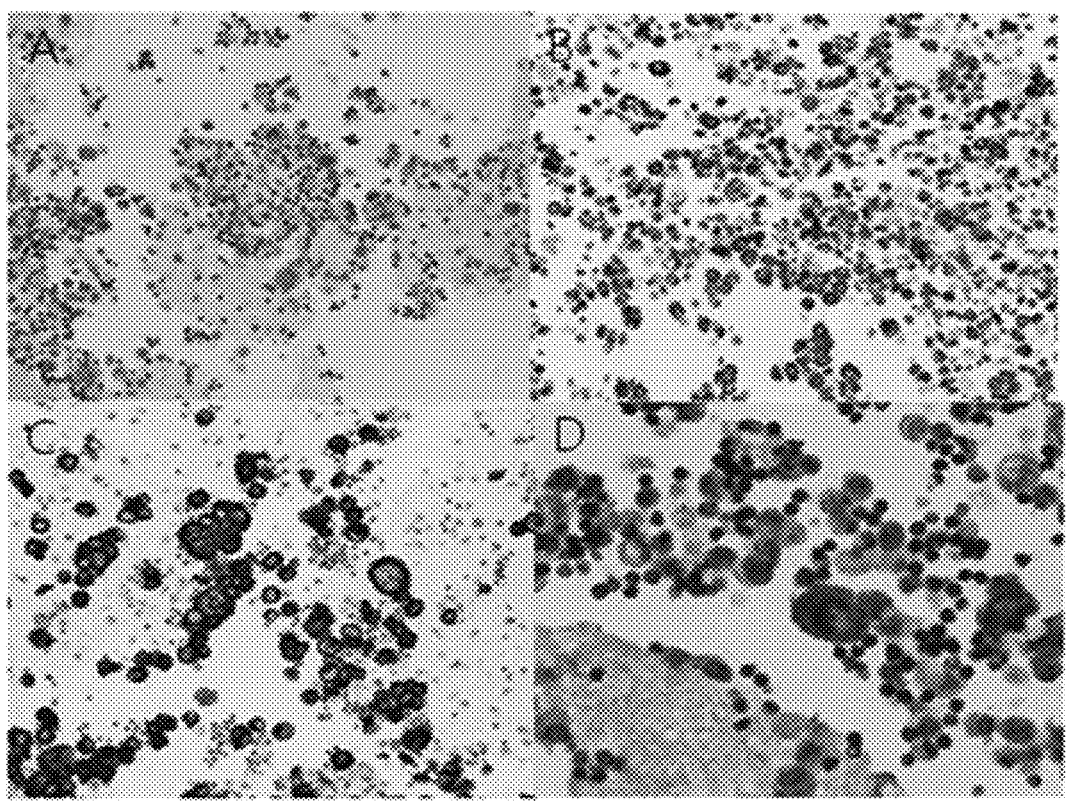
FIG. 5 are microscopic images observing paraffin sections after performing hematoxylin & eosin staining (H&E staining) (200× magnification), vimentin immunohistochemical staining (200×), Pan cytokeratin immunostaining (200×), and PAS histochemical staining (400×), which were prepared from ascitic fluid of a patient with malignant tumor metastasized the peritoneum according to the conventional method for preparing cell block and the present invention.

4) Molecular Biological Analysis—Confirmation of Sensitivity Against FISH and SISH Analysis Against the cell block prepared in the above preparation example 14, perform FISH (fluorescence in situ hybridization) and SISH (silver-enhanced in-situ hybridization) to gene expression of HER2(C-erb B2) according to the conventional methods and compare the results with the above IHC analysis results similar to FIG. 5.

In order to perform FISH analysis for HER2(C-erb B2) gene expression, perform following steps according to manufacturer's description using PathVysion HER2 DNA probe kit (Vysis, Downers Grove, Ill., USA) and Dako Histology FISH Accessory kit. Incubate the cell block prepared by the at 56° C. overnight, deparaffinize in xylol and then perform ethanol dehydration. After soaking it into pretreatment solution and incubating it in water bath at 97° C. for 10 min, treat it with Ready-to-Use Pepsin and incubate them for enzyme treatment at room temperature for 3 min (the cellular sample is collected from endoscopic biopsy or at 37° C. for 6 min (the cellular sample is collected from surgical sample). Then after progressing ethanol dehydration via concentration difference, treat the sample with 10 μl of HER2/CEP17 probe mix, incubate it for denaturation at 80° C. for 5 min, and then put it into Dako Hybridizer and incubate it at 37° C. overnight. Next day, after soaking and incubating the sample in Stringent Wash Buffer in water bath at 65° C. for 10 min, perform ethanol dehydration via concentration difference and treat it with 10 µl of fluorescence mounting medium containing DAPI(4',6-diamino-2-phenylindole).

In addition, in order to perform SIHS for expression of HER2(C-erb B2) automated SHISH analysis was performed on Ventana Benchmark XT (Ventana Medical Systems, Tucson, Ariz., USA) by following steps, wherein INFORM HER2 DNA Probe was visualized according to manufacturer's protocol. At first, against the cell block sample prepared by the above preparation example, deparaffinization, pretreatment, hybridization, stringency wash, signal detection and counterstaining were performed automatically by conventional methods. Wherein the pretreatment was performed for 12 min by using reaction buffer containing ISH protease 3; the hybridization was performed by incubating it at 95° C. for 15 min and then at 56° C. for 6 hr; and the stringency wash was performed by incubating at 72° C. for 8 min 3 times and then incubating for 20 min after treating anti-DNP (dinitrophenol) antibody. Then, the above sample was incubated with HRP (horse radish conjugated) anti-rabbit antibody for 16 min and then sequential silver reactions (Sliver C incubation) was performed for 4 min to detect silver signal of HER2. The control staining was performed by treating it with Hematoxylin II for 8 min and Bluing Reagent for 4 min and the obtained sample was covered with cytosyl mount medium.

Figure 18:
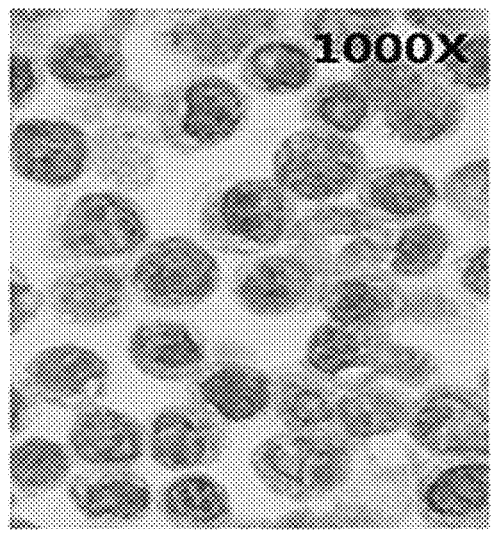
FIG. 18 are result images of FISH(fluorescence in situ hybridization) and SISH(silver in situ hybridization) to cell block sample for cellular microarray according to another example of the present invention.
Figure 18:
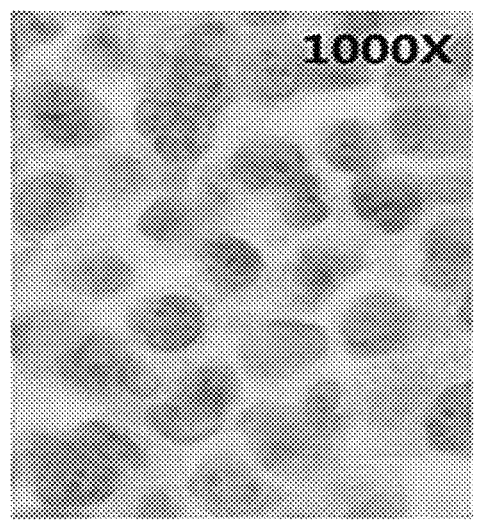
Figure 18:
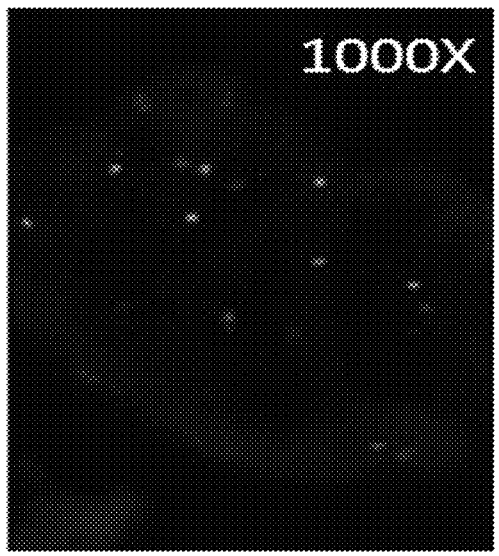
Figure 18:
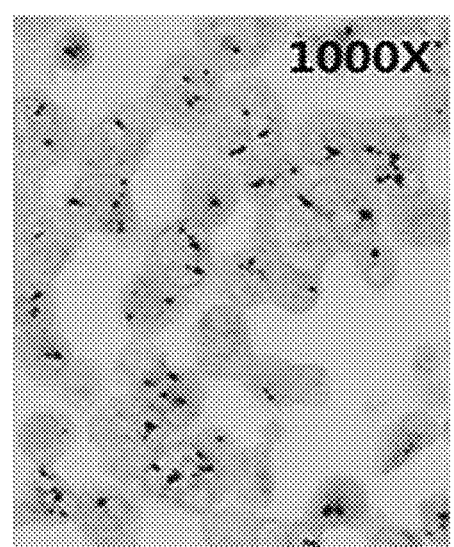

As the results as shown in FIG. 18, it was identified that the cells that had showed negative reaction in IHC analysis (FIG. 5(*b*)) showed negative reaction similarly in FISH (FIG. 5(*c*)) or SISH analysis (FIG. 5(*d*)). Accordingly, it is identified that the cell block for cellular microarray prepared by the present invention had excellent sensitivity in molecular biological analysis including genetic test as well as protein antigenicity in IHC analysis.

INDUSTRIAL APPLICABILITY

The composition for aggregating biological sample, the method for preparing paraffin block using the same, the method for preparing cell block for cellular microarray, and the method for microscopic observation of biological sample using the above paraffin block according to the present invention can be used commonly in various institutes and laboratories performing microscopic observation with tissues or cells, including hospitals, its subsidiary laboratories, medical schools, department of biology, department of biotechnology in college of engineering, and stem cell culture research.

What is claimed is:
1. A composition for aggregating biological sample comprising:
a first composite comprising:
at least one water-soluble polymer selected from the group consisting of polyvinyl alcohol, polyethylene oxide, polyacrylamide, polyvinylpyrrolidon, polyacrylic acid, polyethyleneimine, polyamines, polyamideamine, and polydiallyldimethylammonium chloride, and
distilled water; and
a second composite comprising:
at least one organic solvent selected from the group consisting of alcohol, xylene, and acetone, and
at least one medical adhesive selected from the group comprising cyanoacrylate, fibrin glue, protein glue, polyurethane, and sealant containing PEG (polyethylene glycol),
wherein the first composite and the second composite is used in the amount of 300 to 500 parts by weight based on 100 parts by weight of the sample to be aggregated, respectively.
2. The composition for aggregating biological sample according to claim 1, wherein the water soluble polymer is polyvinyl alcohol; the organic solvent is acetone; and the medical adhesive is cyanoacrylate.
3. The composition for aggregating biological sample according to claim 1, wherein the first composite further comprises carboxymethyl cellulose and dimethyl sulfoxide and the second composite further comprises formalin.
4. The composition for aggregating biological sample according to claim 1, wherein the first composite comprises 1.5~2.0 part by weight of the water soluble polymer based on 100 part by weight of distilled water.
5. The composition for aggregating biological sample according to claim 1, wherein the second composite comprises 100~200 µl of the medical adhesive based on 100 mL of the organic solvent.
6. A composition for aggregating biological sample comprising:
a first composite comprising:
at least one water-soluble polymer selected from the group consisting of polyvinyl alcohol, polyethylene oxide, polyacrylamide, polyvinylpyrrolidon, polyacrylic acid, polyethyleneimine, polyamines, polyamideamine, and polydiallyldimethylammonium chloride, and
distilled water,
wherein the first composite comprises 1.5~2.0 part by weight of the water soluble polymer based on 100 part by weight of distilled water; and
a second composite comprising:
at least one organic solvent selected from the group consisting of alcohol, xylene, and acetone, and
at least one medical adhesive selected from the group comprising cyanoacrylate, fibrin glue, protein glue, polyurethane, and sealant containing PEG (polyethylene glycol), wherein the second composite comprises 100~200 µl of the medical adhesive based on 100 mL of the organic solvent,
wherein the first composite and the second composite is used in the amount of 300 to 500 parts by weight based on 100 parts by weight of the sample to be aggregated, respectively.
7. The composition for aggregating biological sample according to claim 6, wherein the water soluble polymer is polyvinyl alcohol; the organic solvent is acetone; and the medical adhesive is cyanoacrylate.
8. The composition for aggregating biological sample according to claim 7, wherein the first composite further comprises carboxymethyl cellulose and dimethyl sulfoxide and the second composite further comprises formalin.

* * * * *